United States Patent
Kaplan et al.

(10) Patent No.: US 7,761,170 B2
(45) Date of Patent: Jul. 20, 2010

(54) IMPLANTABLE MEDICAL LEAD WITH AXIALLY ORIENTED COILED WIRE CONDUCTORS

(75) Inventors: Paula M. Kaplan, St. Paula, MN (US); Thomas E. Cross, Jr., St. Francis, MN (US); Stephen L. Bolea, Watertown, MN (US); James M. Olsen, Plymouth, MN (US)

(73) Assignee: Medtronic, Inc., Minneapolis, MN (US)

(*) Notice: Subject to any disclaimer, the term of this patent is extended or adjusted under 35 U.S.C. 154(b) by 274 days.

(21) Appl. No.: 11/118,076

(22) Filed: Apr. 29, 2005

(65) Prior Publication Data

US 2006/0089691 A1    Apr. 27, 2006

Related U.S. Application Data

(60) Provisional application No. 60/621,018, filed on Oct. 21, 2004.

(51) Int. Cl.
*A61N 1/05* (2006.01)
(52) U.S. Cl. .................. 607/116; 607/115; 607/119; 607/133; 607/122; 600/372; 600/373; 600/381
(58) Field of Classification Search ......... 607/115–117, 607/119, 122–124, 126, 133, 138; 600/372–374, 600/377, 378, 380, 381
See application file for complete search history.

(56) References Cited

U.S. PATENT DOCUMENTS

| | | |
|---|---|---|
| 3,348,548 A | 10/1967 | Chardack |
| 3,474,791 A | 10/1969 | Bentov |
| 3,572,344 A | 3/1971 | Bolduc |
| 3,596,662 A | 8/1971 | Bolduc |
| 3,804,098 A | 4/1974 | Friedman |
| 3,844,292 A | 10/1974 | Bolduc |
| 4,033,355 A | 7/1977 | Amundson |

(Continued)

FOREIGN PATENT DOCUMENTS

EP    0 004 667    10/1979

(Continued)

OTHER PUBLICATIONS

St. Jude Medical. "Product Performance Report, Cardiac Rhythm Management." Oct. 2007. p. 126.*

(Continued)

*Primary Examiner*—Carl H Layno
*Assistant Examiner*—Michael Chu
(74) *Attorney, Agent, or Firm*—Shumaker & Sieffert, P.A.

(57) ABSTRACT

An implantable lead has a lead body construction designed to accommodate loading forces exerted on the lead body during patient movement. The lead body may be sufficiently stretchable to resist forces that could otherwise cause lead failure, axial migration of the electrodes, anchor damage, or tissue damage. Increasing stretchability of a lead body can also increase the vulnerability of the lead body to flex fatigue, buckling fatigue, kinking, and crush. Therefore, the lead described herein includes conductors that comprise coiled wires positioned substantially parallel to a center axis of the lead. The conductors described herein may be coiled around fibers that limit the axial stiffness of the coiled wires to ensure full recovery from axial loading.

32 Claims, 9 Drawing Sheets

U.S. PATENT DOCUMENTS

| | | | |
|---|---|---|---|
| 4,419,819 A | 12/1983 | Dickhudt et al. | |
| 4,479,500 A | 10/1984 | Smits | |
| 4,484,586 A | 11/1984 | McMickle et al. | |
| 4,559,951 A | 12/1985 | Dahl et al. | |
| 4,572,605 A | 2/1986 | Hess | |
| 4,628,943 A | 12/1986 | Miller | |
| 4,944,088 A | 7/1990 | Doan et al. | |
| 4,972,846 A | 11/1990 | Owens et al. | |
| 5,231,996 A | 8/1993 | Bardy et al. | |
| 5,303,704 A * | 4/1994 | Molacek et al. | 600/377 |
| 5,354,327 A | 10/1994 | Smits | |
| 5,358,517 A * | 10/1994 | Pohndorf et al. | 607/116 |
| 5,454,795 A * | 10/1995 | Samson | 604/526 |
| 5,466,252 A | 11/1995 | Soukup et al. | |
| 5,466,253 A | 11/1995 | Doan | |
| 5,545,203 A * | 8/1996 | Doan | 607/122 |
| 5,591,142 A | 1/1997 | Van Erp | |
| 5,593,433 A | 1/1997 | Spehr et al. | |
| 5,632,734 A | 5/1997 | Galel et al. | |
| 5,674,272 A | 10/1997 | Bush et al. | |
| 5,760,341 A * | 6/1998 | Laske et al. | 174/126.2 |
| 5,796,044 A * | 8/1998 | Cobian et al. | 174/103 |
| 5,836,946 A | 11/1998 | Diaz et al. | |
| 5,845,396 A | 12/1998 | Altman et al. | |
| 5,897,529 A * | 4/1999 | Ponzi | 604/95.04 |
| 5,897,585 A | 4/1999 | Williams | |
| 5,904,680 A | 5/1999 | Kordis et al. | |
| 5,951,539 A * | 9/1999 | Nita et al. | 604/526 |
| 6,018,683 A | 1/2000 | Verness et al. | |
| 6,061,598 A | 5/2000 | Verness et al. | |
| 6,152,912 A * | 11/2000 | Jansen et al. | 604/526 |
| 6,213,995 B1 | 4/2001 | Steen et al. | |
| 6,285,910 B1 | 9/2001 | Verness et al. | |
| 6,295,476 B1 | 9/2001 | Schaenzer | |
| 6,381,835 B1 | 5/2002 | Conger et al. | |
| 6,456,890 B2 | 9/2002 | Pianca et al. | |
| 6,477,427 B1 | 11/2002 | Stolz et al. | |
| 6,501,991 B1 | 12/2002 | Honeck et al. | |
| 6,516,230 B2 | 2/2003 | Williams et al. | |
| 6,551,269 B2 | 4/2003 | Clemens et al. | |
| 6,701,191 B2 | 3/2004 | Schell | |
| 6,757,970 B1 | 7/2004 | Kuzma et al. | |
| 6,823,217 B2 | 11/2004 | Rutten et al. | |
| 6,920,361 B2 | 7/2005 | Williams | |
| 6,978,185 B2 | 12/2005 | Osypka | |
| 2001/0044646 A1 | 11/2001 | Marshall et al. | |
| 2002/0049485 A1 | 4/2002 | Smits | |
| 2002/0072737 A1 | 6/2002 | Belden et al. | |
| 2002/0099430 A1 | 7/2002 | Verness | |
| 2002/0123738 A1* | 9/2002 | Jansen et al. | 604/526 |
| 2002/0143377 A1* | 10/2002 | Wessman et al. | 607/116 |
| 2002/0183822 A1 | 12/2002 | Bodner | |
| 2003/0040666 A1 | 2/2003 | Rutten et al. | |
| 2003/0050680 A1 | 3/2003 | Gibson et al. | |
| 2003/0105505 A1 | 6/2003 | Pianca | |
| 2003/0195602 A1 | 10/2003 | Boling | |
| 2003/0220677 A1* | 11/2003 | Doan et al. | 607/122 |
| 2004/0002727 A1* | 1/2004 | Hwang et al. | 606/194 |
| 2004/0064174 A1 | 4/2004 | Belden | |
| 2005/0027338 A1 | 2/2005 | Hill | |

FOREIGN PATENT DOCUMENTS

| | | |
|---|---|---|
| EP | 0 574 358 B1 | 12/1993 |
| EP | 0 622 089 A2 | 11/1994 |
| EP | 0 672 431 B1 | 9/1995 |
| EP | 0 672 432 B1 | 9/1995 |
| EP | 1 023 915 B1 | 8/2000 |
| WO | WO 00/54833 | 9/2000 |
| WO | WO 01/97903 | 12/2001 |

OTHER PUBLICATIONS

Product Performance Report, St. Jude Medical, Mar. 2003.*
Pacemaker and ICD Encyclopedia, Medtronic, Jan. 2004.*
Shi-ang Xu, M.D. et al., Evaluation of Expandable Leadwires for Pediatric Cochlear Implants, *The American Journal of Otology*, vol. 14, No. 2, pp. 151-160 (Mar. 1993).
U.S. Appl. No..11/119,389 entitled "Implantable Medical Lead With Helical Reinforcement," filed Apr. 29, 2005, by Stephen L. Bolea; Thomas C. Bischoff; Thomas E. Cross, Jr.; and James M. Olsen.
U.S. Appl. No. 11/119,406 entitled "Implantable Medical Lead With Reinforced Outer Jacket," filed Apr. 29, 2005, by James M. Olsen; Thomas E. Cross, Jr.; and Stephen L. Bolea.
U.S. Appl. No. 11/119,416 entitled "Implantable Medical Lead," filed Apr. 29, 2005, by Thomas E. Cross, Jr.; James M. Olsen; and Stephen L. Bolea.
U.S. Appl. No. 11/118,623 entitled "Implantable Medical Lead With Stylet Guide Tube," filed Apr. 29, 2005, by Thomas E. Cross, Jr.; Mary L. Cole; and Stephen L. Bolea.
The International Search Report and the Written Opinion from corresponding PCT Application Serial No. PCT/US2005/037433 mailed Feb. 28, 2006 (11 pages).
International Preliminary Report on Patentability, dated Oct. 6, 2006 for corresponding PCT Application Serial No. PCT/US2005/037433, filed Oct. 19, 2005 (11 pgs).
Office Action dated May 9, 2007 for U.S. Appl. No. 11/118,623 (14 pgs.).
Amendment dated Aug. 8, 2007 for U.S. Appl. No. 11/118,623, (22 pgs.).
Office Action dated May 4, 2007 for U.S. Appl. No. 11/119,389 (9 pgs.).
Amendment dated Aug. 6, 2007 for U.S. Appl. No. 11/119,389 (20 pgs.).
Office Action dated May 4, 2007 for U.S. Appl. No. 11/119,406 (14 pgs.).
Amendment dated Aug. 6, 2007 for U.S. Appl. No. 11/119,406 (24 pgs.).
Office Action dated May 9, 2007 for U.S. Appl. No. 11/119,416 (14 pgs.).
Amendment dated Aug. 8, 2007 for U.S. Appl. No. 11/119,416 (18 pgs.).
Office Action dated Oct. 17, 2007 for U.S. Appl. No. 11/119,389 (6 pgs.).
Response to Office Action dated Dec. 17, 2007 for U.S. Appl. No. 11/119,389 (6 pgs.).
Office Action dated Oct. 23, 2007 for U.S. Appl. No. 11/118,623 (13 pgs.).
Response to Office Action dated Dec. 21, 2007 for U.S. Appl. No. 11/118,623 (15 pgs.).
Office Action dated Jan. 24, 2008 for U.S. Appl. No. 11/119,389 (10 pgs.).
Office Action dated Oct. 23, 2007 for U.S. Appl. No. 11/119,406 (16 pgs.).
Office Action dated Oct. 29, 2007 for U.S. Appl. No. 11/149,416, (12 pgs.).
Response to Office Action dated Jan. 29, 2008 for U.S. Appl. No. 11/119,416 (17 pgs.).
Office Action dated Feb. 11, 2008 for U.S. Appl. No. 11/118,623 (10 pgs.).
Response to Office Action dated May 12, 2008 for U.S. Appl. No. 11/118,623 (15 pgs.).
Response to Office Action dated Apr. 24, 2008 for U.S. Appl. No. 11/119,389 (20 pgs.).
Office Action dated Jul. 22, 2008 for U.S. Appl. No. 11/119,389 (8 pgs.).
Responsive Amendment dated Sep. 22, 2008 for U.S. Appl. No. 11/119,389 (13 pgs.).
Office Action dated Sep. 16, 2008 for U.S. Appl. No. 11/118,623 (12 pgs.).
Request for Continued Examination and Responsive Amendment dated Dec. 16, 2008 for U.S. Appl. No. 11/118,623 (16 pgs.).

Office Action dated Nov. 26, 2008 for U.S. Appl. No. 11/119,416 (13 pgs.).
Responsive Amendment dated Apr. 27, 2009 for U.S. Appl. No. 11/119,416 (13 pgs.).
Office Action dated Feb. 26, 2009 for U.S. Appl. No. 11 118,623 (9 pgs.).
Responsive Amendment dated May 26, 2009 for U.S. Appl. No. 11/118,623 (12 pgs.).
Office Action dated Sep. 10, 2009 for U.S. Appl. No. 11/118,623 (12 pgs.).

* cited by examiner

IMPLANTABLE MEDICAL LEAD WITH AXIALLY ORIENTED COILED WIRE CONDUCTORS

This application claims the benefit of U.S. provisional application No. 60/621,018, filed Oct. 21, 2004, the entire content of which is incorporated herein by reference.

TECHNICAL FIELD

The invention relates to implantable medical devices and, more particularly, implantable medical leads.

BACKGROUND

A variety of implantable medical devices (IMDs) are available to monitor physiological conditions within a patient, deliver therapy to a patient, or both. Typically, an IMD is coupled to one or more implantable leads that carry electrodes to sense physiological electrical activity or deliver electrical stimulation. Cardiac pacemakers and cardioverter-defibrillators, for example, are coupled to one or more intravenous or epicardial leads that include sensing electrodes to sense cardiac electrical activity, stimulation electrodes to deliver pacing, cardioversion or defibrillation pulses, or a combination of sensing and stimulation electrodes.

Neurostimulation systems also include implantable leads for delivery of neurostimulation therapy to patients to treat a variety of symptoms or conditions such as chronic pain, tremor, Parkinson's disease, multiple sclerosis, spinal cord injury, cerebral palsy, amyotrophic lateral sclerosis, dystonia, torticollis, epilepsy, urinary incontinence, fecal incontinence, sexual dysfunction, obesity, or gastroparesis or other gastric mobility disorders. An implantable neurostimulator delivers electrical stimulation pulses via electrodes carried by leads implanted proximate to the spinal cord, pelvic nerves, stomach, or gastrointestinal tract, or within the cranium of a patient, e.g., for deep brain stimulation or occipital nerve stimulation.

As a patient implanted with an IMD moves, some regions of the body may expand and contract, resulting in changes in length. The movement may exert high loading forces on anchors, leads, lead extensions, or body tissue. These forces may cause lead failure, axial migration of electrodes, anchor damage, or tissue damage. The patient may experience pain or operational failure or performance degradation of the IMD.

SUMMARY

In general, the invention is directed to an implantable medical lead having a lead body with axially oriented coiled wire conductors. The lead has a construction designed to accommodate loading forces exerted on the lead body during patient movement. In some embodiments, the lead body may be sufficiently stretchable to resist forces that could otherwise cause lead failure, axial migration of the electrodes, anchor damage, or tissue damage. Increased stretchability of a lead body can also increase the vulnerability of the lead body to flex fatigue, buckling fatigue, kinking, and crush. Therefore, the lead described herein also may include conductors comprising coiled wires positioned substantially parallel to a center axis of the lead.

The lead body may include a variety of features that reduce the axial stiffness of the lead without significantly impacting the operation and structural integrity of lead components, such as electrodes, conductors and insulators. However, the conductors described herein may be coiled around fibers that limit the axial elongation of the coiled wires to ensure full recovery from axial loading. Several embodiments of a lead are described herein. For example, a lead body may comprise a low durometer outer jacket and/or conductors with a low modulus of elasticity, providing increased stretchability.

In some embodiments, the lead may also include a coiled wire stylet guide to provide enhanced column strength. The coiled wire stylet guide may or may not be electrically conductive. A helical reinforcement also may be added to the lead to create a lead body that is resistant to flex fatigue, buckling fatigue, kinking and crush. Furthermore, a coiled wire may be embedded between a first insulative layer and a second insulative layer of an outer jacket of the lead body to improve column stiffness and kink resistance. Utilizing one or more of the above features, the lead is able to accommodate changes in length associated with typical patient movement while maintaining structural integrity of the lead.

In one embodiment, the invention is directed to an implantable medical lead for use with an implantable medical device. The lead comprises a lead body that defines a center axis, and multiple conductors located inside the lead body. At least one of the conductors includes a coiled wire defining a lumen with a center axis substantially parallel to the center axis of the lead body.

In another embodiment, the invention is directed to an implantable medical device comprising a housing, an implantable pulse generator, within the housing, that generates electrical stimulation pulses, and an implantable lead. The lead extends from the housing, and comprises a lead body that defines a center axis, multiple electrodes, and multiple conductors located inside the lead body. At least one of the conductors includes a coiled wire defines a lumen with a center axis substantially parallel to the center axis of the lead body. The conductors electrically couple the electrodes to the implantable pulse generator.

The invention also contemplates methods of use and fabrication of an implantable lead and implantable medical device.

The invention may be capable of providing one or more advantages. For example, a lead constructed in accordance with the invention may result in reduced mechanical loading on tissue anchor points, implantable lead extensions, the implantable lead itself, and the IMD during typical patient movement. In addition, the lead may improve resistance to flex fatigue, buckling fatigue, kinking, and crush. These features may also provide advantages beyond strengthening the lead. For example, a coiled wire stylet guide may provide improved column steerability as well as enhanced stylet insertion and withdrawal. In some embodiments, straight wire conductors may be combined with the coiled stylet guide to achieve low conductor impedance while maintaining stylet maneuverability within the coiled guide. Furthermore, a fiber within a coiled wire conductor may be provided to limit axial stiffness of the coiled wire to prevent over-extension and deformation of the conductor.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
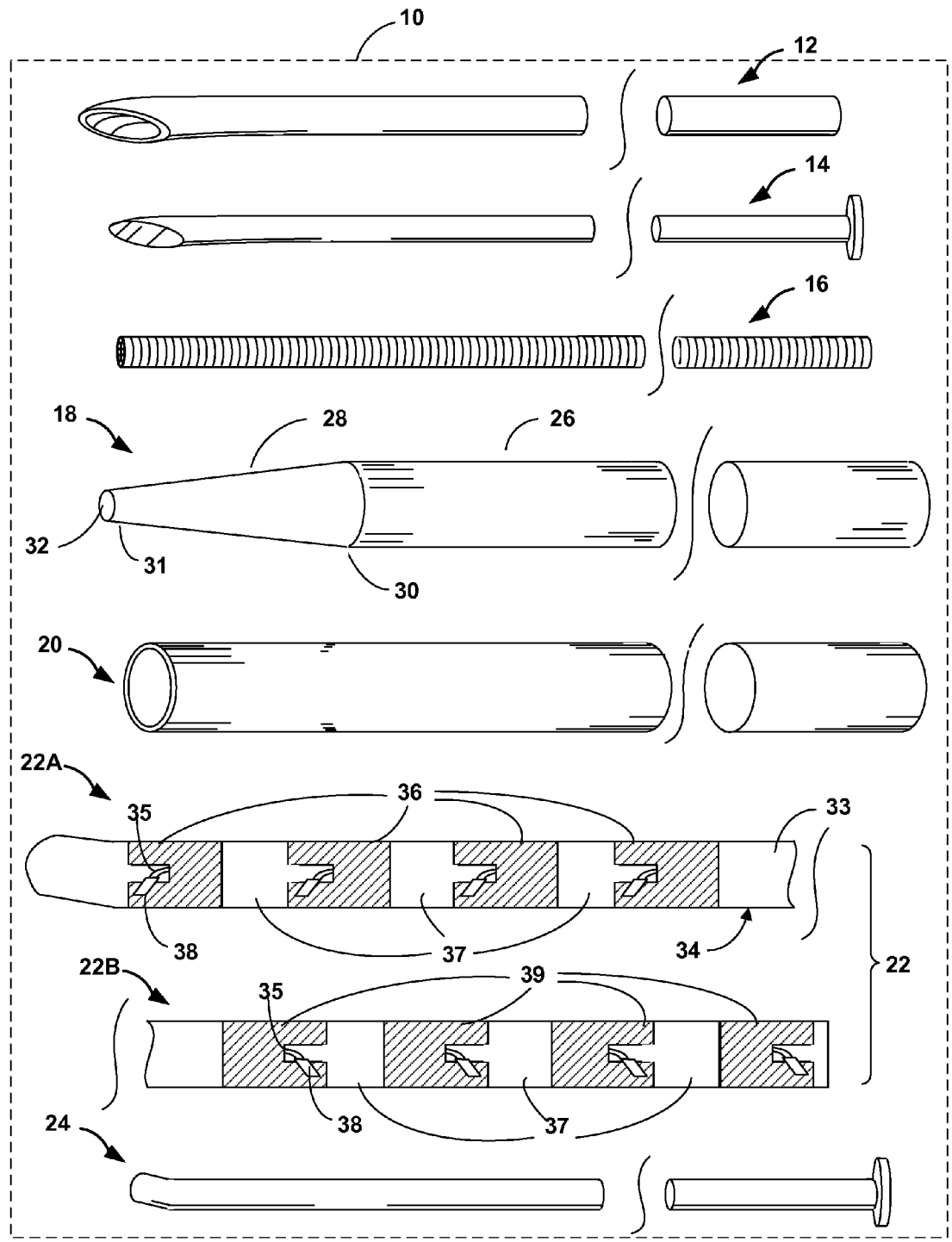
FIG. 1 is a diagram illustrating a stimulation lead introducing kit, which includes components for percutaneously implanting a stimulation lead.

FIG. 1 is a diagram illustrating a stimulation lead introducing kit 10, which includes components for percutaneously implanting a stimulation lead in accordance with the invention. In other embodiments, the lead may be surgically implanted. As shown in FIG. 1, kit 10 includes a needle 12, a needle stylet 14, a guidewire 16, a dilator 18, a sheath 20, a stimulation lead 22, and a lead stylet 24. Lead 22 has a lead body that is constructed to accommodate loading forces exerted on the lead during patient movement. FIG. 1 shows a distal portion 22A and a proximal portion 22B of lead 22. In some embodiments, lead 22 may be sufficiently stretchable to resist forces that could otherwise cause lead failure, axial migration of the electrodes, anchor damage, or tissue damage.

Lead 22 may be coupled to an implantable medical device (IMD), either directly or via a lead extension. As a patient moves, portions of the patient's body in which an IMD may be implanted change in length. For example, the fascial surface dorsal to the lumbar spine elongates approximately 3.7 inches (9.4 cm) in a typical individual from a neutral or standing position to a fully flexed or bent over position as measured from the iliac crest to the area near the spinous process of the first lumbar vertebra. Conventional lead bodies are unable to accommodate some changes in length within a patient's body, even with the addition of subcutaneous strain relief loops in the lead and/or lead extensions. Consequently, some lead bodies may be prone to lead failure or performance degradation due to fractures or electrical shorting, axial migration of electrodes coupled to the lead body, anchor damage, and/or tissue damage at anchor points.

Lead 22 may include a lead body constructed to exhibit a reduced axial stiffness that permits the lead body to better accommodate changes in length along a patient's body. In one embodiment, for example, the lead body of lead 22 exhibits an axial stiffness of no greater than 5.0 pounds/inch/inch (0.35 kg/cm/cm), more preferably between approximately 5.0 pounds/inch/inch and 1.5 pounds/inch/inch (0.105 kg/cm/cm), and even more preferably between approximately 3.3 pounds/inch/inch (0.23 kg/cm/cm) and 1.5 pounds/inch/inch. These ranges of axial stiffness may be achieved by selection of appropriate materials and design features for lead 22. For example, in some embodiments, lead 22 may combine low durometer outer jacket materials with structural features such as low filar count coiled conductors to enhance stretchability, while also incorporating additional structural features such as a coiled stylet guide and helical reinforcement wires for structural integrity.

A reduced axial stiffness in the above range promotes increased stretchability in the lead body to better accommodate changes in length along the patient's body. A medical lead body with an axial stiffness in the above ranges may permit an axial elongation of approximately five percent to approximately thirty percent, and more preferably approximately ten percent to thirty percent, without breakage or degradation of performance. In some cases, the enhanced stretchability may substantially eliminate lead failure due to fractures or electrical shorting, axial migration of electrodes coupled to the lead body, anchor damage, and/or tissue damage at anchor points. The above axial stiffness values are expressed in pounds/inch/inch, rather than simply pounds/inch, as the lead body may have different lengths, depending upon the model and manufacturer, as well as different degrees of elongation during use. As an example, however, the lead body of lead 22 may generally correspond to a lead body with a length of approximately 12 inches to 14 inches (30 cm to 36 cm), and more preferably approximately 13 inches (33 cm), at an elongation of approximately 1 inch (2.54 cm). In some embodiments, the lead body of lead 22 may have longer lengths, e.g., for application in which no lead extension is used to couple to an IMD. In these cases, the lead body may be up to approximately 120 cm in length.

Several embodiments of leads are described herein. For example, a lead body may comprise a low durometer outer jacket and/or conductors with a low modulus of elasticity. In addition, the lead may comprise a coiled wire stylet guide to provide enhanced column strength and steerability while improving stylet insertion and withdrawal. The lead may also include a helical reinforcement wire to create a lead body that is resistant to flex fatigue, buckling fatigue, axial displacement, kinking and crush. Furthermore, a coiled wire may be embedded between a first insulative layer and a second insulative layer within an outer jacket of the lead body to improve column stiffness and kink resistance. In this way, the lead is able to accommodate changes in length within the body associated with typical patient movement while maintaining structural integrity. Some of the features described herein may be applied not only to leads, but also leads that are not significantly stretchable.

With further reference to FIG. 1, a stimulation lead 22 may be percutaneously implanted in the epidural region proximate a spine of a patient. Although kit 10 depicts the deployment of a lead for purposes of spinal cord neurostimulation, other applications are contemplated. For example, a lead as described herein may be used in a variety of sensing and therapy applications such as spinal cord neurostimulation, sacral neurostimulation, deep brain stimulation, and cardiac sensing and stimulation, e.g., for pacing, cardioversion or defibrillation. However, spinal cord neurostimulation will be described for purposes of illustration.

The elements in kit 10 are not necessarily shown to scale in FIG. 1. The diagram of FIG. 1 depicts the distal ends and proximal ends of the parts in kit 10 at the left and right, respectively. In general, a "distal" end will refer to the first end of a component that is introduced into the patient, whereas the "proximal" end generally extends outside of the body for manipulation by medical personnel.

Needle 12 has a lumen to receive needle stylet 14. In some instances, needle 12 may take the form of a modified Tuohy needle, which has an opening that is angled, e.g., approximately 45 degrees, so that an instrument passing through the needle exits through the needle at an angle. Needle stylet 14 fills the lumen of needle 12 to prevent coring in the tissue of a patient when needle 12 is inserted into the patient.

Guidewire 16 is an elongated, flexible instrument that is steerable to permit deployment of the guidewire to a desired "target" site, e.g., within the epidural region. In practice, guidewire 16 may be inserted through needle 12 and steered through the epidural region to the target site for neurostimulation therapy. Guidewire 16 prepares a path so that a stimulation lead introducer, formed by dilator 18 and sheath 20, can reach the target site by advancing over guidewire 16.

Dilator 18 has a cross-section that produces a widened path through body tissue for deployment of stimulation lead 22. Sheath 20 fits over dilator 18 to form the stimulation lead introducer. In particular, sheath 20 permits passage of stimulation lead 22 when dilator 18 is not present in sheath 20, i.e., upon withdrawal of dilator 18.

Stimulation lead 22 may include a cylindrical structure with at least one ring electrode 36 to provide stimulation to tissue within a patient, as shown in FIG. 1. In other embodiments, the stimulation lead may comprise a paddle lead. FIG. 1 depicts a distal end of stimulation lead 22, including a lead body 33, which carries electrodes 36 that function as tissue-stimulating electrodes. A proximal end of lead body 33 is coupled to an implantable medical device (IMD) (not shown), such as a neurostimulator that generates neurostimulation energy for delivery via electrodes 36. In particular, proximal portion 22B of lead 22 includes electrical contacts 39 for electrical contact with terminals within an IMD.

Lead 22 defines a lumen that receives lead stylet 24. Lead stylet 24 may comprise a wire sized to fit within a stylet lumen of lead 22. In some embodiments, lead stylet 24 may have an outer diameter of approximately 0.012 inches to 0.010 inches (0.03 cm to 0.025 cm). Lead stylet 24 may be substantially steerable to permit deployment of stimulation lead 22 to a desired "target" site within the epidural region. In practice, lead stylet 24 may be inserted through lead 22 to steer lead 22 to the target site for neurostimulation therapy.

In some embodiments, lead 22 may have a length of approximately 12 to 14 inches (30 to 36 cm), and more preferably approximately 13 inches (33 cm). At an elongation of approximately 1 inch (2.54 cm), lead body 33 exhibits an axial stiffness of no greater than 0.50 pounds/inch (0.09 kg/cm), more preferably between approximately 0.5 pounds/inch and 0.15 pounds/inch (0.03 kg/cm), and even more preferably between approximately 0.33 pounds/inch (0.06 kg/cm) and 0.15 pounds/inch. In this manner, lead 22 allows typical patient movement without causing lead failure or performance degradation due to axial migration, anchor damage, and/or tissue damage at anchor points.

The distal portion 22A of stimulation lead 22 shown in FIG. 1 includes four ring electrodes 36 and a spacer 37 placed between electrodes 36. A similar arrangement may be provided in proximal portion 22B with electrical contacts 39. Electrodes 36 may be formed from a variety of electrically conductive, biocompatible materials. Example electrode materials includes platinum and platinum iridium. Spacer 37 may comprise a polyurethane or silicone material, or an alloy of silicone and polyurethane. In various embodiments, stimulation lead 22 may take the form of an octad lead including eight ring electrodes or a quad lead including four ring electrodes, shown in FIG. 1. However, stimulation lead 22 may be designed to accommodate any number of electrodes. A line of neurostimulation leads utilizing ring electrodes is commercially available from Medtronic, Inc. of Minneapolis, Minn.

Lead body 33 of lead 22 may comprise an outer jacket 34. Lead body 33 carries conductors 35 within a lumen created by outer jacket 34. Conductors 35 connect electrodes 36 to the IMD coupled to the proximal end of lead body 33. As shown in FIG. 1, a set of distal tissue-stimulating electrodes 36 in distal portion 22A are coupled to a set of proximal electrical contacts 39 in proximal portion 22B via conductors 35. Distal electrodes 36 deliver electrical stimulation pulses to tissue within the patient. Proximal contacts 39 are coupled to an implantable pulse generator (IPG) within the IMD to receive the stimulation pulses. As an example, conductors 35 may comprise braided strand wire (BSW) cables.

The stranded wire used to create the BSW cables for conductors 35 may comprise a silver core. As an example, the stranded wire may comprise MP35N™ alloy, which is a biocompatible, nonmagnetic, nickel-cobalt-chromium-molybdenum alloy with high strength and corrosion resistance, with a silver core to improve conductance. However, the silver may create difficulties when welding conductors 35 to electrodes 36, which may comprise platinum iridium (PtIr).

As one solution, a crimp tube 38 comprising a weldable material may be crimped onto the end of each of conductors 35. Crimp tube 38 may then be laser welded to electrodes 36 at distal lead portion 22A and proximal lead portion 22B. Crimp tube 38 may comprise a material that substantially eliminates silver from the weld. In some cases, crimp tube 38 may comprise platinum. A similar arrangement may be used for electrical contacts 39. In other embodiments, a variety of other solutions may be utilized to connect conductors 35 to electrodes 36.

Outer jacket 34 of lead body 33 may be made of an extruded or molded material, such as a polyurethane or silicone material, or alloys of silicone and polyurethane. The material may include a substantially low durometer material, substantially similar to an elastomer, to accommodate changes in length within a patient's body. For purposes of illustration, in one exemplary embodiment, assuming lead 22 is approximately 13 in (33 cm) in length and at an elongation of approximately 1 inch (2.54 cm), the material of outer jacket 34 may have a modulus of elasticity between approximately 0.37 pounds/inch$^2$ (0.026 kg/cm$^2$) and 0.1 pounds/inch$^2$ (0.007 kg/cm$^2$), and more preferably between approximately 0.2 pounds/inch$^2$ (0.014 kg/cm$^2$) and 0.1 pounds/inch$^2$.

Conductors 35, within lead 22 conforming to the above listed dimensions, may comprise an axial stiffness between approximately 0.13 pounds/inch (0.023 kg/cm) and 0.05 pounds/inch (0.009 kg/cm), and more preferably between approximately 0.08 pounds/inch (0.014 kg/cm) and 0.05 pounds/inch. Conductors 35 comprising BSW cables may provide increased flexibility. Coiling or helically winding conductors 35 allows conductors 35 to elongate or stretch. In particular, the individual coils tend to narrow in diameter as they are stretched along the longitudinal axis of lead 22. Furthermore, the coiled or helically wound conductors may form a lumen for insertion and withdrawal of lead stylet 24. To increase an overall elasticity of lead body 33, conductors 35 may comprise a low number of filars per coil. With a low number of filars, e.g., two to four per coil, concentric conductor coils can be used to achieve a required number of conductors. Furthermore, conductor coils may be designed with a high coil diameter to wire diameter ratio. In other embodiments, the conductors may comprise flat wire wound into coils.

When lead 22 is implanted within a patient, outer jacket 34 of lead body 33 may become hydrated by bodily fluids. This can alter physical properties of a material comprising outer jacket 34, such as a polyurethane material. Outer jacket 34 may become more stretchable when in the hydrated state. The altered physical properties may include modulus of elasticity, durometer, impact resistance, and the like.

Enhancing the elasticity of lead body 33 reduces forces on lead 22, lead extensions, anchors, and body tissue at anchor sites, which can cause the patient pain and/or render the IMD inoperable. In either case, not accommodating changes in length within the patient's body can be detrimental to the patient's health. However, increasing stretchability of lead body 33 can also increase the lead body's vulnerability to flex fatigue, buckling fatigue, kinking, and crush.

In order to maintain structural integrity of lead body 33 while reducing overall axial stiffness, one or more reinforcing structures may be added to lead 22. For example, coiled wire may form an inner stylet guide tube. The coiled wire stylet guide may be electrically conductive or nonconductive, and increases column strength and resistance to kinking while providing a smooth reliable path for lead stylet 24.

A reinforcement wire may be helically wound around conductors 35 to prevent bi-lateral collapse of lead body 33 during buckling. In some cases, the helically wound reinforcement wire may create a helical channel in which conductors 35 may lie. Furthermore, a coiled wire may be included within outer jacket 34 or between two thin jacket extrusions external to outer jacket 34. The embedded wire may provide protection against kinking of lead body 33, in a manner similar to the wire often embedded in a vacuum cleaner hose.

Figure 2:
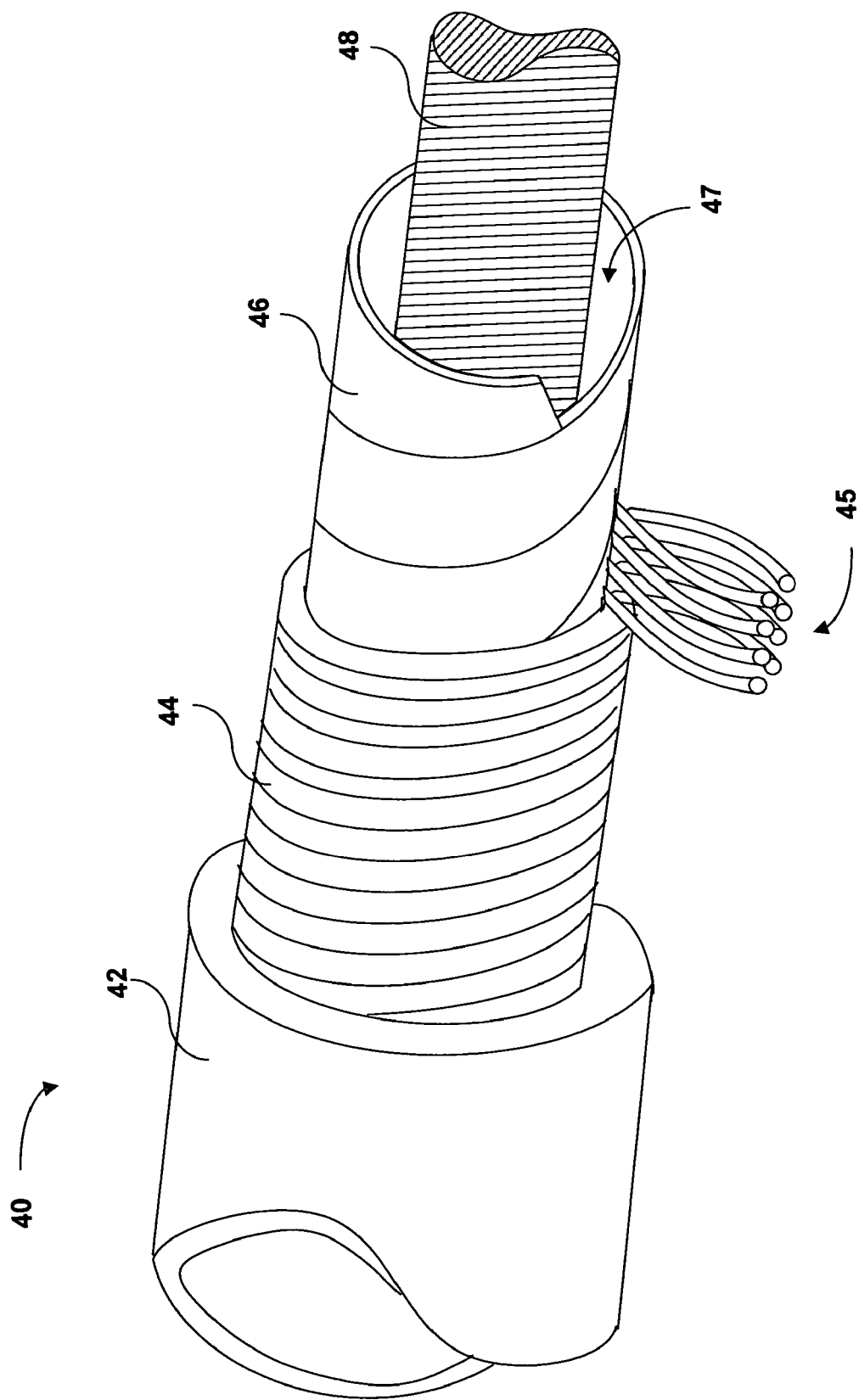
FIG. 2 is a schematic diagram illustrating a cutaway view of an implantable medical lead for use with an implantable medical device according to an embodiment of the invention.

FIG. 2 is a schematic diagram illustrating a cutaway view an implantable medical lead 40 for use with an implantable medical device according to an embodiment of the invention. Lead 40 may comprise a stretchable lead substantially similar to lead 22 (FIG. 1). Accordingly, lead 40 may be percutaneously implanted using a stimulation lead introducing kit substantially similar to kit 10 illustrated in FIG. 1. Lead 40 may include at least one electrode to provide stimulation to a patient. The electrode may include a ring electrode or an arrangement of electrodes on a paddle lead.

Lead 40 includes an outer jacket 42 and a coiled stylet guide 46 positioned within a lumen formed by outer jacket 42. Coiled stylet guide 46 may be formed by flat or cylindrical wires, which may be electrically conductive or nonconductive. Outer jacket 42 may comprise an external diameter of approximately 0.045 to 0.055 inches (0.114 to 0.14 cm), and more preferably approximately 0.052 inches (0.13 cm). Stylet guide 46 may comprise an external diameter of approximately 0.012 to 0.020 inches (0.03 to 0.05 cm), and more preferably approximately 0.016 inches (0.04 cm). A set of conductors 45 wraps around stylet guide 46 to form one or more conductor coils 44. In the illustrated embodiment, lead 40 comprises an octad lead with eight conductors included in set of conductors 45. In other embodiments, lead 40 may comprise a quad lead including four electrodes or another type of lead including any number of electrodes.

In some embodiments, lead 40 provides enhanced stretchability to prevent lead failure, axial migration, anchor damage, and/or tissue damage at anchor points during typical patient movement. Outer jacket 42 may be made of an extruded or molded material, e.g., a polyurethane material, with a substantially low durometer. Conductors 45 may comprise braided strand wire (BSW) cables that provide increased flexibility.

Conductors 45 may be constructed as BSW cables wound into a helix. Coiling or helically winding conductors 45 into conductor coil 44 allows conductors 45 to elongate or stretch as lead 40 experiences axial loading forces during use. Helically wound conductors 45 may provide desirable axial compliance as well as needed bend-flex fatigue life. In a case of severe buckling, the helically wound conductors 45 may collapse, binding the conductors and concentrating the bend into a small radius. To address this problem, as described above, a reinforcement wire may be helically wound with the wound conductors 45 in a way that prevents bilateral collapse of the structure during buckling. The wound reinforcement wire also may be helically extruded, forming a helical channel in which the conductors reside, as will be described in greater detail herein.

Coiled wire stylet guide 46 creates a lumen 47 to receive a stylet 48. In some cases, stylet 48 comprises a wire with a diameter between approximately 0.012 inches and 0.01 inches (0.03 cm and 0.025 cm). Stylet 48 may be inserted into lumen 47 of stylet guide 46 to steer lead 40 to a target site within a patient's body. The coil design of stylet guide 46 eases the insertion and withdrawal of stylet 48 by forming a smooth path along which stylet 48 slides. In addition, coiled wire stylet guide 46 may enhance steerability of lead 40, which increases accuracy when positioning lead 40 within a patient.

At a distal end of lead 40, not shown, stylet guide 46 may be sealed such that stylet 48 cannot extend beyond the distal end of lead 40. Sealing the distal end of stylet guide 46 decreases the probability of inadvertently puncturing epidural tissue and causing a "wet tap," or cerebral spinal fluid (CSF) leak, which is an event that may cause severe headaches or, if the leak is severe, may cause neurological damage. A CSF leak may occur if stylet 48 extends beyond stylet guide 46 into the epidural region proximate the spine of a patient, causing a puncture in the dura membrane of the epidural region.

During typical patient movement, the lead 40 may experience compressive buckling. Conventional leads may comprise an extruded plastic stylet guide. In that case, the plastic stylet guide may be prone to bi-lateral collapse, which creates a flat and wide cross-section. If the kink formed in the plastic stylet guide forces the conductors into a sharp bend radius, this cyclical loading may cause lead failure. In contrast, coiled stylet guide 46 can resist such problems.

FIG. 2 illustrates a coiled wire stylet guide 46 comprising an electrically passive helically wound wire. In the illustrated embodiment, coiled stylet guide 46 comprises a flat or ribbon wire. In other embodiments, coiled stylet guide 46 may comprise a round wire or a wire with a rectangular cross section. Stylet guide 46 may comprise a metal wire, such as an MP35N wire. In some embodiments, stylet guide 46 may be insulated with a polymeric material, such as ethylene-tetrafluoroethylene (ETFE). Other examples of insulative materials include polytetrafluoroethylene (PTFE), modified PTFE, and polyimide, as well as polyurethane, silicone, and polyester. Although the wire in stylet guide 46 may be electrically inactive, insulating the coiled wire stylet guide 46 reduces abrasion with conductors 45.

The wire is wound in a helical fashion to form a substantially cylindrical shape for stylet guide 46. As discussed above, stylet guide 46 comprises a diameter of approximately 0.012 inches to 0.020 inches (0.03 cm and 0.05 cm), and preferably approximately 0.016 inches (0.04 cm). In general, stylet guide 46 comprises a diameter small enough to allow conductor coil 44 to fit between coiled stylet guide 46 and outer jacket 42 and large enough to resist crushing and collapse.

The helically coiled structure separates between adjacent turns to allow stylet guide 46 to bend, either at a corner or during compression, while maintaining a substantially round cross-section. Stylet guide tube 46 is coiled in an opposite direction of conductors 45. This may prevent conductors 45 from being pinched by coils of stylet guide tube 46. Coiled wire stylet guide 46 is able to substantially withstand crushing and collapse by preventing cross-sectional flattening and forcing a larger bend radius than traditional plastic stylet guides. In some embodiments, coiled wire stylet guide 46 may comprise a single wire strand, i.e., a mono-filar cable. In this case, stylet guide 46 may experience less torsional stress during bending than a multi-filar cable.

Figure 3:
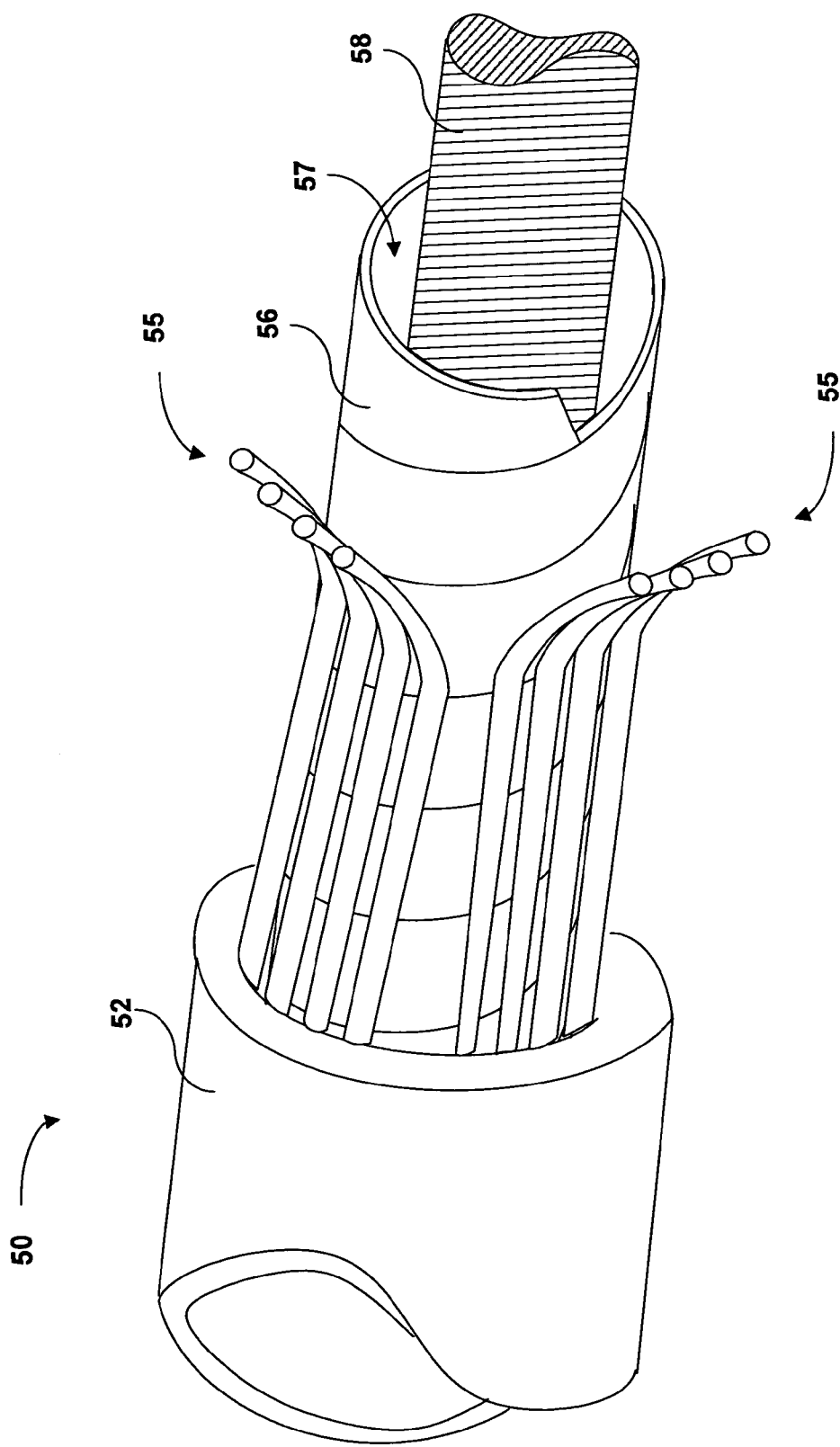
FIG. 3 is a schematic diagram illustrating a cutaway view of another implantable medical lead according to an embodiment of the invention.

FIG. 3 is a schematic diagram illustrating a cutaway view of another implantable medical lead 50 for use with an implantable medical device according to an embodiment of the invention. Lead 50 may be substantially similar to lead 22 from FIG. 1 and lead 40 from FIG. 2. Lead 50 includes an outer jacket 52 and a coiled wire stylet guide 56 positioned within a lumen formed by outer jacket 52. Coiled wire stylet guide 56 creates a lumen 57 to receive a stylet 58. Outer jacket 52 and stylet guide 56 may comprise diameters substantially similar to outer jacket 42 and stylet guide 46 described in reference to FIG. 2. A set of conductors 55 lies axial to stylet guide 56, also within the lumen formed by outer jacket 52. In the illustrated embodiment, lead 50 comprises an octad lead with eight conductors included in set of conductors 55. In other embodiments, lead 50 may comprise a quad lead including four electrodes or another type of lead including any number of electrodes.

As in the example of FIG. 2, conductors 55 may comprise braided strand wire (BSW) cables. As an example, the stranded wire may comprise MP35N alloy. In the illustrated embodiment of FIG. 3, however, conductors 55 comprise straight wires that extend axially along the length of lead 50. The straight orientation of conductors 55 serves to reduce the overall length of the conductors, relative to coiled conductors, and thereby reduces conductor impedance. Decreasing impedance of conductors 55 may significantly increase battery longevity of an IMD to which lead 50 is coupled.

FIGS. 4A-4E are schematic diagrams illustrating exemplary cross-sectional views of leads with axially positioned conductors. Each of the illustrated leads in FIGS. 4A-4E may be substantially similar to lead 50 from FIG. 3. In the illustrated embodiments, the leads comprise octad leads that include eight conductors. In other embodiments, each of the leads may comprise a quad lead including four conductors or another type of lead comprising any number of conductors.

Figure 4A:
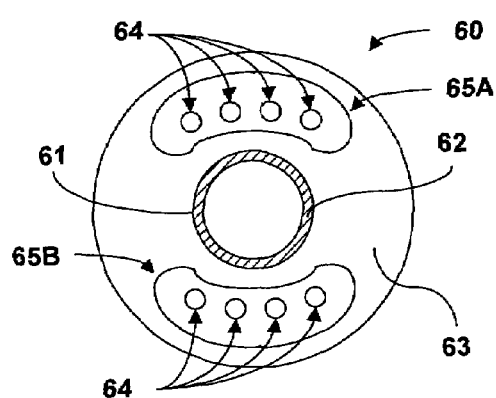
FIGS. 4A-4E are schematic diagrams illustrating exemplary cross-sectional views of leads with axially positioned conductors.

FIG. 4A illustrates a lead 60 comprising a coiled wire stylet guide 62 substantially similar to coiled wire stylet guide 46 (FIG. 2) and coiled wire stylet guide 56 (FIG. 3). In the illustrated embodiment, an electrically nonconductive ribbon wire forms coiled wire stylet guide 62. The ribbon wire may be formed from a metallic alloy such as MP35-N, stainless steel, titanium, titanium alloy, tantalum, tantalum alloy, nitinol or other metals or metallic alloys. Lead 60 includes a conventional extruded outer jacket 63 with an expanded extruded inner wall defining lumen 61. Outer jacket 63 may be formed from polyurethane or silicone, or an alloy of silicone and polyurethane. Stylet guide 62 is encapsulated within lumen 61 of outer jacket 63. In this way, a conventional outer jacket 63 may be modified to incorporate stylet guide 62.

The stylet guide tube 62 may be assembled into the lead by sliding stylet guide tube 62 into the lumen 61 of the outer jacket 63. The stylet guide tube 62 may be incorporated in the lead body assembly during the extrusion forming process of the outer jacket 63. Another option would be to insert mold the stylet guide tube 62 into the outer jacket, using a suitable mold incorporating core pins used to form lumens 65A, 65B, or other lumens in the examples of FIGS. 4B-4E. Coiled wire stylet guide 62 eases insertion and withdrawal of a stylet from lumen 61 and may enhance steerability of lead 60. In addition, stylet guide 62 allows lead 60 to maintain a substantially circular cross section during bending to resist bi-lateral collapse or kinking.

Outer jacket 63 also forms a first conductor lumen 65A and a second conductor lumen 65B through which conductors 64 may pass axially to lead 60. In the illustrated embodiment, first lumen 65A includes four of conductors 64 and second lumen 65B also includes four of conductors 64. Conductors 64 are positioned axially, rather than coiled, along the length of outer jacket 63 of lead 60. Outer jacket 63 may comprise a low durometer material to decrease the stiffness of lead 60. For example, outer jacket 63 may comprise a polyurethane or silicone material, or an alloy of silicone and polyurethane. Conductors 64 may include BSW cable to increase flexibility of lead 60.

Figure 4B:
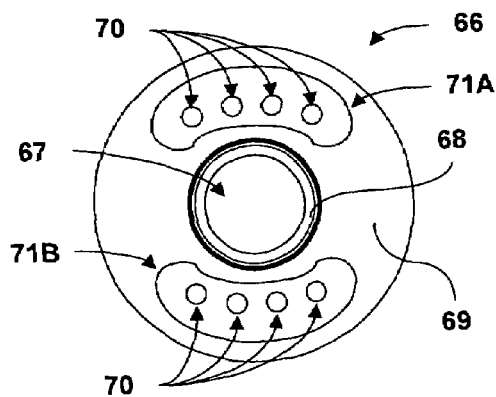

FIG. 4B illustrates another lead 66 comprising a coiled wire stylet guide 68. In the illustrated embodiment, a passive insulated metal wire forms coiled wire stylet guide 68. For example, stylet guide 68 may comprise a coiled silver core wire coated with urethane insulation. Other examples of insulating materials for the silver core wire include polyurethane, ethylene-tetrafluoroethylene (ETFE), polytetrafluoroethylene (PTFE), modified PTFE, polyimide, polyimide, silicone, and polyester.

For example, stylet guide 68 may include an MP35N wire. Lead 66 includes an extruded outer jacket 69 flowed to contact the coating of stylet guide 68. Stylet guide 68 forms a lumen 67 that receives a stylet, which steers lead 66 to a therapy delivery position. Stylet guide 68 also increases a resistance of lead 60 to collapse during compression by forcing a larger bend radius.

Outer jacket 69 also forms a first conductor lumen 71A and a second conductor lumen 71B through which conductors 70 may pass axially to lead 66. In the illustrated embodiment, first lumen 71A includes four of conductors 70 and second lumen 71B also includes four of conductors 70, all of which are axially oriented along the length of lead 66. Again, as in the example of FIG. 4A, outer jacket 63 may comprise a low durometer material, such as polyurethane, to increase stretchability of lead 66. Conductors 70 may comprise BSW to increase flexibility of lead 66.

Figure 4C:
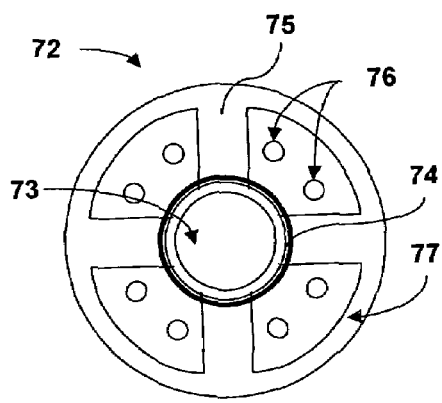

FIG. 4C illustrates another lead 72 comprising a coiled wire stylet guide 74 with axially positioned conductors. In the illustrated embodiment, a passive metal wire coated with an insulation material forms coiled wire stylet guide 74. As in the example of FIG. 4B, stylet guide 74 may comprise a MP35N wire coated with urethane insulation. Lead 72 includes an extruded outer jacket 75 flowed to contact the insulative coating of stylet guide 74. Stylet guide 74 forms a lumen 73 that receives a stylet. Outer jacket 75 forms four conductor lumens 77 through which conductors 76 may pass axially along the length of lead 72. In the illustrated embodiment, each of conductor lumens 77 includes two of conductors 76. Again, outer jacket 75 may comprise a polyurethane material with a low durometer, while conductors 76 may comprise BSW to increase flexibility of lead 72.

Figure 4D:
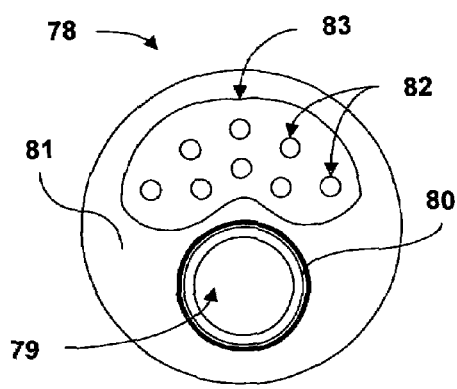

FIG. 4D illustrates another lead 78 comprising a coiled wire stylet guide 80 with axially positioned conductors. In the illustrated embodiment, a passive metal wire coated with an insulation forms coiled wire stylet guide 80. For example, stylet guide 80 may comprise a MP35N wire coated with urethane insulation. Lead 78 includes an extruded outer jacket 71 flowed to the coating of stylet guide 80. Stylet guide 80 forms a lumen 79 that receives a stylet. In the example of FIG. 4D, outer jacket 81 forms a single conductor lumen 83 through which all eight of conductors 82 may pass axially to lead 78.

Figure 4E:
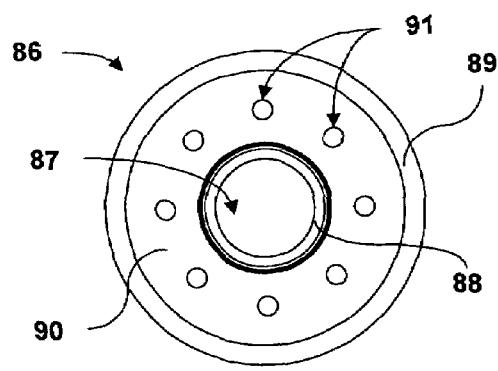

FIG. 4E illustrates another lead 86 comprising a floating coiled wire stylet guide 88 and axially positioned conductors. In the illustrated embodiment, lead 86 includes an outer jacket 89 that forms a lumen 90, which receives stylet guide 88. Conductors 91 are positioned between outer jacket 89 and stylet guide 88. Conductors 91 may comprise flexible BSW. Neither stylet guide 88 nor conductors 91 are anchored within lumen 90 of outer jacket 89. Instead, outer jacket 89 contains stylet guide 88 and conductors 91, such that the conductors are sandwiched between the outer jacket and the stylet guide. An electrically conductive or nonconductive metal wire coated with a lubricating insulation forms coiled wire stylet guide 88. For example, stylet guide 88 may comprise a MP35N wire coated with ETFE. Other examples of insulative materials include polytetrafluoroethylene (PTFE), modified PTFE, and polyimide, as well as polyurethane, silicone, and polyester. The insulation around the coil turns in stylet guide 88 reduces abrasion with conductors 91.

Figure 5:
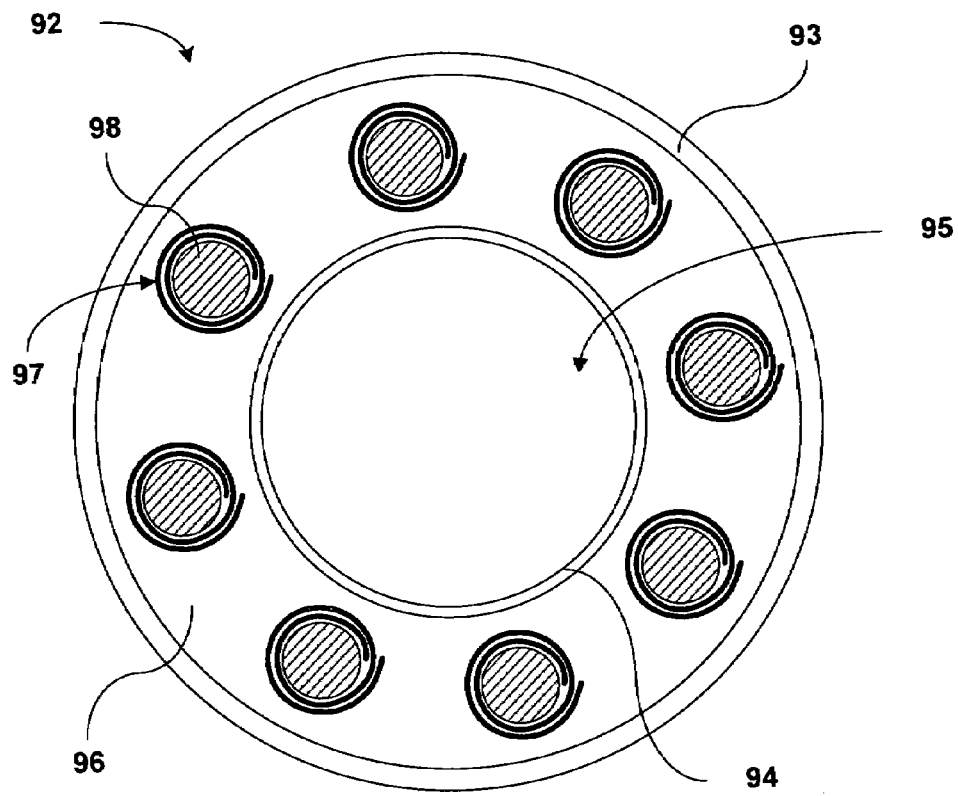
FIG. 5 is a schematic diagram illustrating another exemplary cross-sectional view of a lead with axially oriented coiled wire conductors.

FIG. 5 is a schematic diagram illustrating an exemplary cross-sectional view of a lead 92 with axially oriented coiled wire conductors 97. Coiled wire conductors 97 are axially oriented in the sense that they each form a conductor that extends axially along the length of lead 92. In the example of FIG. 5, although each individual coiled wire conductor 97 includes a single- or multi-filar coil, none of the conductors are actually coiled about the central axis of lead 92. Conductors 97 preferably are formed in tight coils, such that each of the conductors forms a substantially continuous cylindrical shape.

Lead 92 illustrated in FIG. 5 may be substantially similar to lead 50 from FIG. 3. In the illustrated embodiment of FIG. 5, lead 92 comprises an octad lead that includes eight conductors. In other embodiments, lead 92 may comprise a quad lead including four conductors or another type of lead comprising any number of conductors.

In FIG. 5, lead 92 includes an outer jacket 93 that forms a lumen 96, which receives a stylet guide tube 94. Stylet guide tube 94 may be substantially similar to coiled wire stylet guide 46 (FIG. 2) and coiled wire stylet guide 56 (FIG. 3). In other cases, stylet guide tube 94 may comprise a conventional plastic stylet guide tube. Stylet guide tube 94 forms a lumen 95 that receives a stylet. Conductors 97 are positioned between outer jacket 93 and stylet guide 94, at different angular positions about the central axis of lead 92. Hence, conductors 97 extend along the length of lead 92 substantially parallel to the center axis defined by outer jacket 93. Yet, each axially oriented conductor 97 is formed by a single- or multi-filar coil.

In some embodiments, as described herein, lead 92 provides enhanced stretchability to prevent lead failure, axial migration, anchor damage, and/or tissue damage at anchor points during typical patient movement. Outer jacket 93 may comprise a low durometer material to decrease the stiffness of lead 92. For example, outer jacket 93 may comprise a polyurethane or silicone material, or an alloy of silicone and polyurethane.

Conductors 97 may comprise one or more BSW cables that provide increased flexibility. The stranded wire used to create the BSW cables for conductors 97 may comprise a silver core. As an example, the stranded wire may comprise MP35N™ alloy, which is a biocompatible, nonmagnetic, nickel-cobalt-chromium-molybdenum alloy with high strength and corrosion resistance, with a silver core to improve conductance. In other cases, conductors 97 may comprise platinum iridium (PtIr) wires or tantalum tungsten (TaW) wires.

Conductors 97 may be constructed as BSW cables wound into a helix. Coiling or helically winding conductors 97 allows the conductors to elongate or stretch as lead 92 experiences axial loading forces during use. Helically wound conductors 97 may provide desirable axial compliance as well as desirable bend-flex fatigue life. However, in a case of severe buckling, some of the helically wound conductors 97 may collapse, causing cross-sectional flattening and concentrating the coiled wires into a small bend radius. Furthermore, conductors 97 may over-extend longitudinally during lead stretching, causing permanent deformation of the coiled wires.

To address these problems, conductors 97 are coiled around fibers 98. Each of conductors 97 defines a lumen which receives fiber 98. Fiber 98 may comprise a composite that includes materials such as fluoropolymer, modified fluoropolymer, polyester, nylon, liquid crystal polymer (LCP), modified LCP, ultra high molecular weight (UHMW) polyethylene, or Kevlar® fiber. Kevlar® fiber is commercially available from DuPont. In general, fiber 98 provides the coiled wire with structural integrity and limits displacement of conductor 97 along the length of lead 92.

Fiber 98 prevents bilateral collapse of the coiled wire during buckling. More specifically, fiber 98 substantially reduces an amount of cross-sectional flattening and forces a larger bend radius. When lead 92 is in use, the coiled wire of conductor 97 may stretch when a patient moves. Fiber 98 comprises a material composite that is extendable and allows fiber 98 to elongate along with conductor 97. However, fiber 98 also limits an axial stiffness and extension of conductor 97 to prevent over-extension of conductors 97 due to axial loading. In addition, fiber 98 preferably is elastic, so that the fiber 98 returns to its original length upon release of the axial loading. In this way, fiber 98 ensures that the coiled wire of conductor 97 is not over-extended, and fully recovers after reaching a maximum axial extension.

For example, the coiled wire of conductor 97 has an axial stiffness of no greater than 5.0 pounds/inch/inch (0.35 kg/cm/cm), more preferably between approximately 5.0 pounds/inch/inch and 1.5 pounds/inch/inch (0.105 kg/cm/cm), and even more preferably between approximately 3.3 pounds/inch/inch (0.23 kg/cm/cm) and 1.5 pounds/inch/inch. In some embodiments, fiber 98 limits the axial stiffness of the coiled wire of conductor 97 to no less than approximately 1.5 pounds/inch/inch (0.105 kg/cm/cm).

In the illustrated embodiment, each of conductors 97 comprises a single-filar coil. Each coiled wire connects a tissue-stimulating electrode on a distal end of lead 92 and an electrical contact on a proximal end of lead 92. In this case, lead 92 includes eight conductors 97 that each couple to an electrode. In other embodiments, lead 92 may include conductors that comprise one or more multi-filar coils. For example, four conductors may be coiled into a single multi-filar coil. In this way, lead 92 may include eight electrodes, but carry only two multi-filar coils within lumen 96 of outer jacket 93.

Neither stylet guide tube 94 nor conductors 97 need to be anchored within lumen 96 of outer jacket 93. Instead, outer jacket 93 contains stylet guide tube 94 and conductors 97, such that the conductors are sandwiched between outer jacket 93 and stylet guide tube 94. Fibers 98 comprise distal ends and proximal ends. In some cases, the distal ends of each of fibers 98 may be attached to the distal end of lead 92. In other cases, the proximal ends of each of fibers 98 may be attached to the proximal end of lead 92. Furthermore, fibers 98 may be attached to both the distal and the proximal ends of lead 92. In other embodiments, where fibers 98 are not attached to lead 92, conductors 97 are substantially free to float within lumen 96 of outer jacket 93.

Attachment of proximal and distal ends of fibers 98 to lead 92, in combination with limitations on the axial stretchability of the fibers 98, can ensure that lead 92 does not over-stretch coiled conductors 97. In this manner, fibers 98 can provide a stretch-limit for lead 92 that prevents damage to coiled conductors 97. Although fibers 98 are disposed within lumens defined by coiled conductors 97, one or more fibers alternatively or additionally may be formed elsewhere within lead 92 to limit extension of the overall lead. For example, one or more fibers 98 may be placed between outer jacket 93 and stylet guide tube 94, and extend axially along the length of lead 92. In this case, each fiber 98 may be coupled to outer jacket 93, stylet guide tube 94, or both to limit extension of lead 92. Each fiber 98 may be coupled, e.g., at proximal and distal ends, to outer jacket 93, stylet guide tube 94, or both.

In some embodiments, the diameter of the lumen defined by each coiled wire conductor 97 may vary over the length of lead 92. For example, a coiled wire conductor 97 may present a larger diameter along substantially all of the lead 92, but a reduced diameter adjacent a distal tip of the lead so that the lead is more flexible in the region in which electrodes are positioned. The outer diameter of coiled wire conductor 97 contributes to the outer diameter of lead 92. Hence, the diameter of coiled wire conductor 97 may change along the length of lead 92 so that the outer diameter of the lead transitions from a larger, more extensible lead body to a smaller, more flexible distal electrode end.

Figure 6:
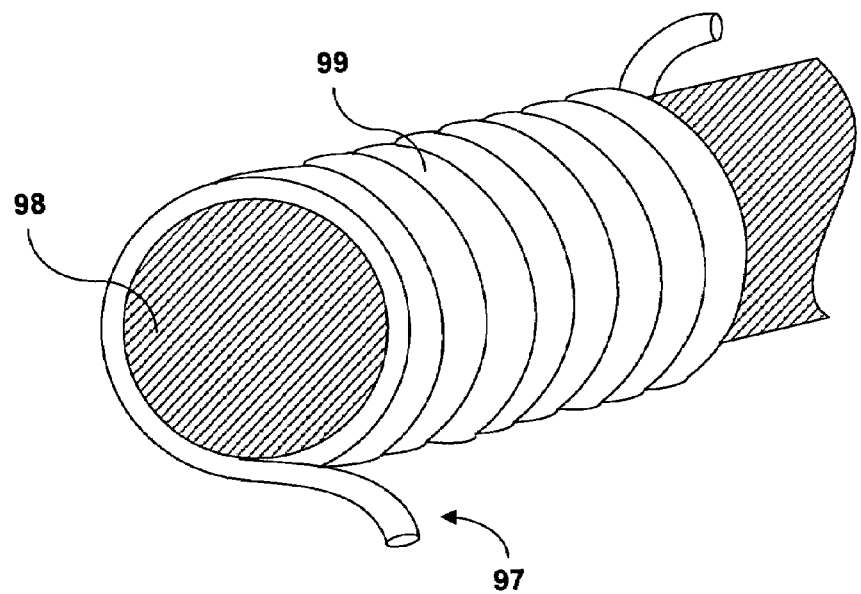
FIG. 6 is a schematic diagram illustrating a cutaway view of a coiled wire conductor.

FIG. 6 is a schematic diagram illustrating a cutaway view of coiled wire conductor 97 from lead 92 of FIG. 5. Conductor 97 coils around fiber 98 to create a coil 99. In some embodiments, an insulative outer member may be included around coil 99. In this way, conductor 97 may be redundantly insulated not only with direct urethane insulation, but also by the insulative outer member. The insulative outer member may reduce abrasion with stylet guide tube 94 and other conductors within lumen 96 of outer jacket 93. The insulative outer member may comprise a low durometer material, such as a polyurethane or silicone material, or an alloy of silicone and polyurethane.

Coil 99 of conductor 97 may comprise an external diameter of approximately 0.004 to 0.021 inches (0.01 to 0.053 cm), more preferably approximately 0.004 to 0.016 inches (0.01 to 0.04 cm), and even more preferably approximately 0.006 to 0.015 inches (0.015 to 0.038 cm). Fiber 98 may comprise an external diameter of approximately 0.002 to 0.015 inches (0.005 to 0.038 cm), more preferably approximately 0.002 to 0.010 inches (0.005 to 0.025 cm), and even more preferably approximately 0.005 to 0.007 inches (0.013 to 0.018 cm).

The outer diameter of coil 99 may depend on the number of conductors included in coil 99. In addition, the distance between adjacent turns in coils (i.e., the pitch) may also depend on the number of conductors included in coil 99. For example, a single-filar coil may comprise a pitch of approximately 0.002 to 0.015 inches (0.005 to 0.038 cm). A multi-filar coil may comprise a pitch of approximately 0.003 to 0.025 inches (0.008 to 0.064 cm). Any number of conductors may be coiled around fiber 98 as long as the multi-filar coil maintains an outer diameter small enough to fit between stylet guide tube 94 and outer jacket 93.

Figure 7:
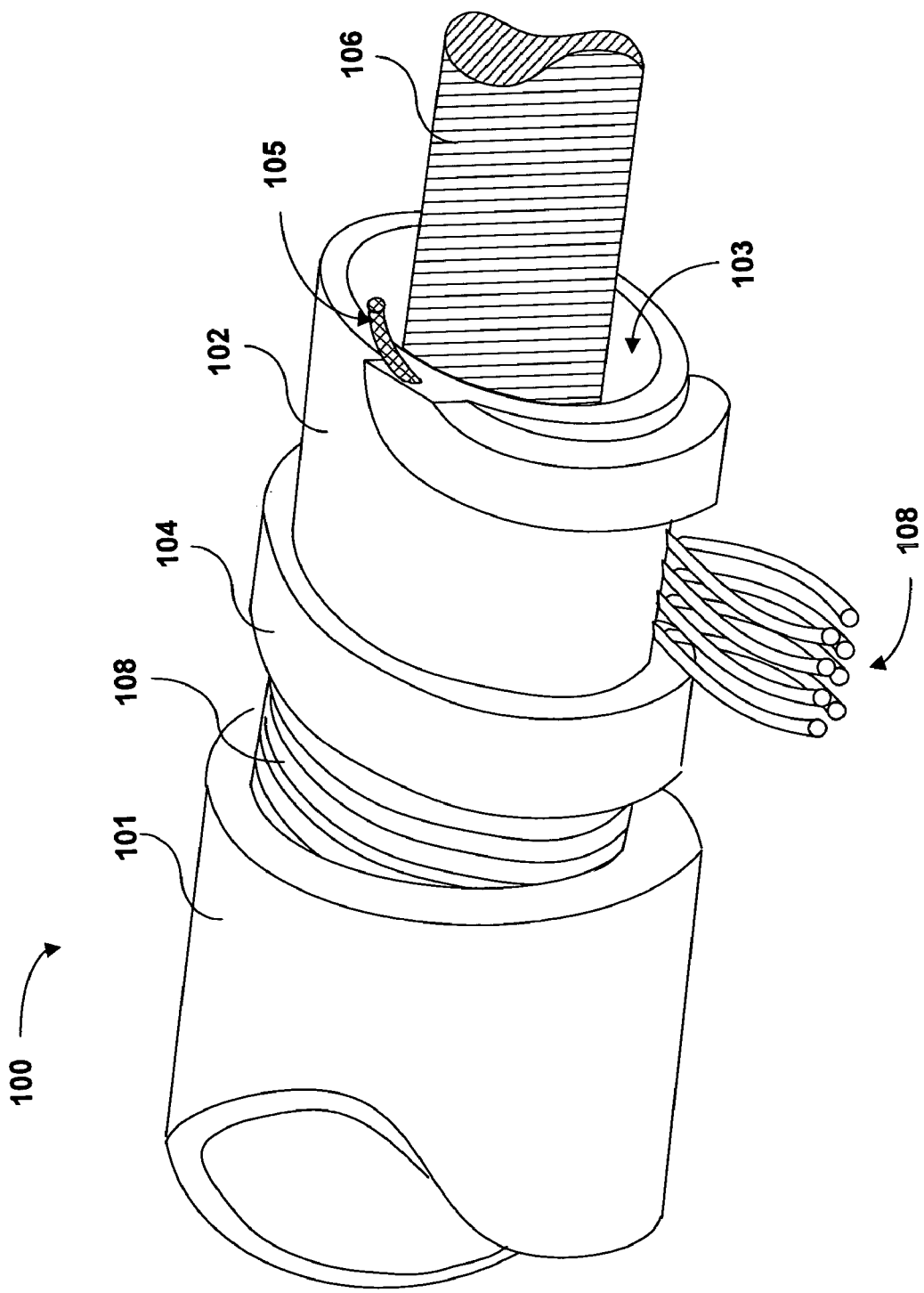
FIG. 7 is a schematic diagram illustrating a cutaway view of another implantable medical lead according to an embodiment of the invention.

FIG. 7 is a schematic diagram illustrating a cutaway view of another implantable stretchable medical lead 100 for use with an IMD according to an embodiment of the invention. Lead 100 may be percutaneously implanted using a stimulation lead introducing kit substantially similar to kit 10 illustrated in FIG. 1. Lead 100 includes an outer jacket 101, a helical reinforcement 102 and conductors 108 coiled about the reinforcement. Helical reinforcement 102 includes a raised acme thread 104 with an embedded reinforcement wire 105. Alternatively, in some embodiments, thread 104 may have a trapezoidal cross-section. For illustrative purposes, stylet 106 is also shown, but is not part of lead 100 itself. Conductors 108 wrap around helical reinforcement 102 in substantial alignment with the raised acme thread 104. In particular, raised acme thread 104 defines a helical trough or channel between adjacent turns to accommodate conductors 108.

Lead 100 differs from lead 40 shown in FIG. 2 and lead 50 shown in FIG. 3 in that lead 100 does not comprise a separate stylet guide tube. The body of helical reinforcement 102 has a one-piece design that includes a substantially cylindrical tube and helical thread 104 on the outer surface of the tube. The body of helical reinforcement 102 may consist of machined or extruded urethane, for example, such that acme thread 104 is integrally formed with the cylindrical tube or is wound onto surface of the cylindrical tube and bonded in place. Stylet 106 fits inside a lumen 103 formed from the cylindrical shape of helical reinforcement 102.

As discussed previously, e.g., in the description of FIG. 1, reducing the axial stiffness of a medical lead may provide a variety of benefits. The embodiment of the invention depicted in FIG. 7 may have a relatively low axial stiffness. For example, the body of helical reinforcement 102 may consist of urethane or other materials having a low modulus of elasticity, providing increased stretchability. Likewise, outer jacket 101 may also consist of urethane having a low modulus of elasticity.

Helical reinforcement wire 105 and conductors 108 do not experience significant axial strain as lead 100 experiences strain from patient movement, because helical reinforcement wire 105 and conductors 108 are helically wrapped around the cylindrical shape of helical reinforcement 102. As lead 100 experiences strain, the helical reinforcement 102 is deformed, reducing the diameter of the cylindrical shape of helical reinforcement 102, which allows the coils of conductors 108 and reinforcement wire 105 to extend under relatively low forces, without experiencing significant axial tension.

Reducing the axial stiffness of a medical lead can also increase the lead vulnerability to flex fatigue, buckling fatigue, kinking, and crush. Each of these circumstances may result in increased conductor resistivity or even conductor failure. However, stretchable medical lead 100 may not only have a relatively low modulus of elasticity, but its design may also reduce conductor failure due to flex fatigue, buckling fatigue, kinking, and crush.

Helical reinforcement 102, including reinforcement wire 105 embedded in acme thread 104, may generally improve the structural integrity of lead 100. For example, helical reinforcement 102 may provide protection against kinking of lead 100 and bi-lateral collapse of helical reinforcement 102. The helical shape of reinforcement wire 105 resists bilateral collapse, buckling fatigue, flex fatigue, crush, and kinking, and reinforcement wire 105 provides structural support for lead 100. Use of a reinforcement wire, as described herein, may provide a very durable construction, particularly for a small profile lead, and supports axial compliance that may help compensate for implant technique error and allow for greater patient comfort.

Reinforcement wire 105 may comprise a metallic alloy wire formed from MP35-N, stainless steel, titanium, titanium alloy, tantalum, tantalum alloy, nitinol or other metals or metallic alloys. Further, wire 105 may be redundantly insulated not only by acme thread 104, but also directly with urethane insulation. While reinforcement wire 105 does not carry a current, insulating reinforcement wire 105 may decrease the chance that reinforcement wire 105 would propagate a short among conductors 108.

The outer surface of acme thread 104 may touch the inner surface of outer jacket 101, but acme thread 104 is not otherwise attached to outer jacket 101. In this manner, conductors 108 fit in the helical trough-like space formed between helical reinforcement 102 and outer jacket 101. This may prevent conductors 108 from bunching or kinking within lead 100, even if lead 100 experiences repeated elongation and contraction caused by patient movement. In addition, conductors 108 may not overlap acme thread 104. While thread 104 is illustrated as an acme thread in the example of FIG. 7, other threads may also be used.

Figure 8:
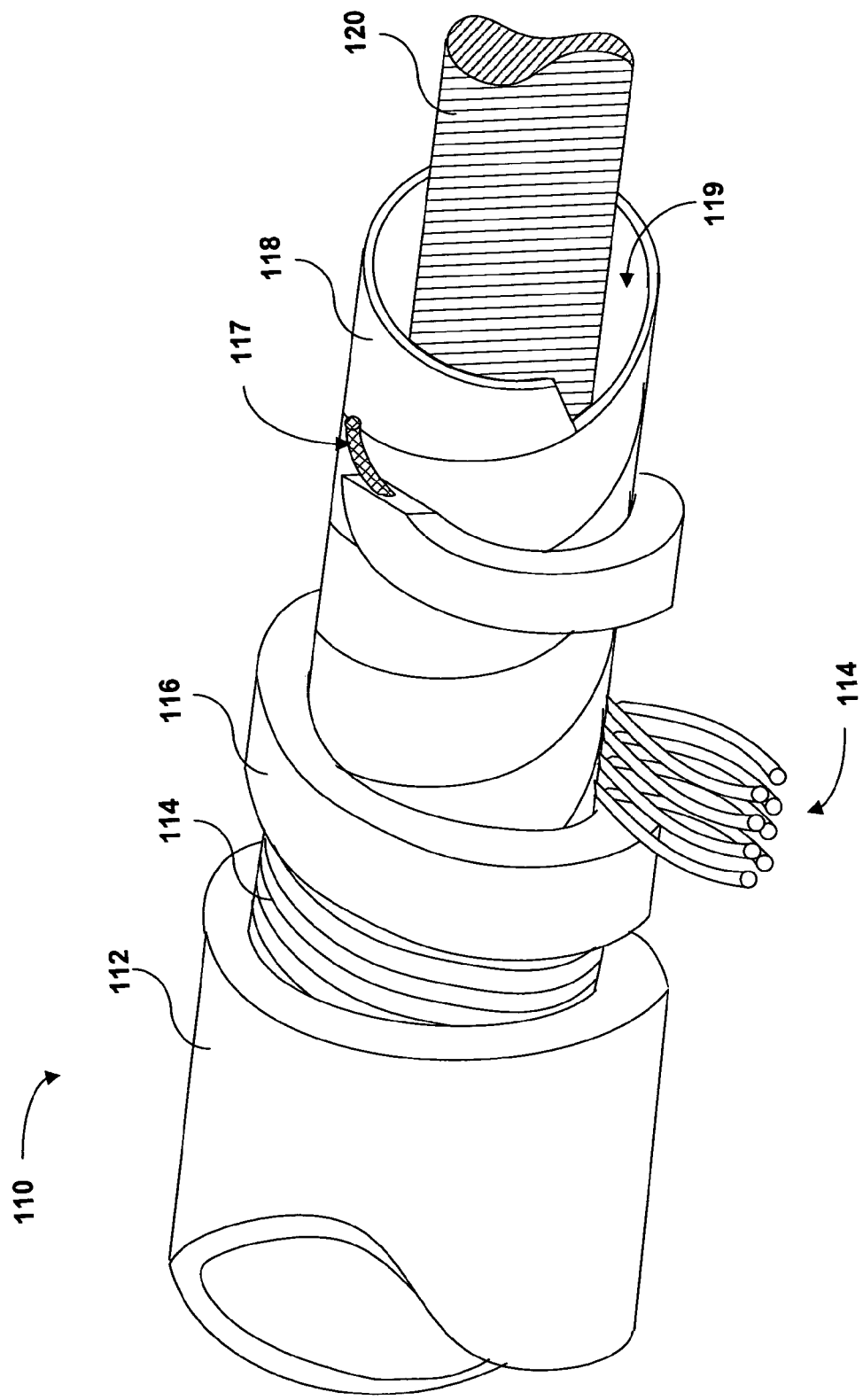
FIG. 8 is a schematic diagram illustrating a cutaway view of another implantable medical lead according to an embodiment of the invention.

FIG. 8 is a schematic diagram illustrating a cutaway view of another implantable stretchable medical lead 110 for use with an implantable medical device according to an embodiment of the invention. Lead 110 may be percutaneously implanted using a stimulation lead introducing kit substantially similar to kit 10 illustrated in FIG. 1. Lead 110 includes an outer jacket 112, a helical reinforcement wire 116, conductors 114, and a stylet guide tube 118. For illustrative purposes, stylet 120 is also shown inserted through lumen 119 formed by stylet guide tube 118, but is not part of lead 110 itself. Conductors 114 wrap around stylet guide tube 118 in substantial alignment with helical reinforcement wire 116.

Lead 110 functions in a substantially similar manner to the embodiment of the invention depicted in FIG. 7. Consequently, lead 110 has a low axial stiffness for the same general reasons lead 100 of FIG. 7 has a low axial stiffness. As opposed to lead 100 of FIG. 7, lead 110 includes a separate stylet guide tube 118. Stylet guide tube 118 is formed by an electrically inactive (or active) coiled flat wire, for example, as described with reference to FIG. 2. In other embodiments of the invention, different stylet guide tubes may be used.

As lead 110 experiences axial strain, the coils of stylet guide tube 118 separate under relatively low stresses, but the cylindrical shape of stylet guide tube 118 is maintained to provide structural support. Stylet guide tube 118 is coiled in an opposite direction of helical reinforcement wire 116 and conductors 114. This may prevent helical reinforcement wire 116 and conductors 114 from being pinched by coils of stylet guide tube 118. In addition, conductors 114 may not overlap helical reinforcement wire 116 and helical reinforcement wire 116 may not overlap conductors 114.

Helical reinforcement wire 116 includes an insulated metallic wire 117 embedded for structural support. For example, helical reinforcement wire 116 may provide protection against kinking and bi-lateral collapse of lead 110. Helical reinforcement wire 116 includes insulated metallic wire 117, which may comprise a metal such as MP35-N, stainless steel, titanium, titanium alloy, tantalum, tantalum alloy, nitinol or other metals or metallic alloys. While insulated metallic wire 117 may not carry a current, insulation may decrease the chance that wire 117 would propagate a short among conductors 114.

Helical reinforcement wire 116 has a rectangular cross section and may be formed from polyurethane, polysulfone, polypropylene or PEEK. The outer surface of helical reinforcement wire 116 may touch the inner surface of outer jacket 112. In this manner, conductors 114 fit in a helical space formed between stylet guide tube 118 and outer jacket 112. This may prevent conductors 114 from bunching or kinking within lead 110, even if lead 110 experiences repeated elongation and contraction caused by patient movement.

Figure 9:
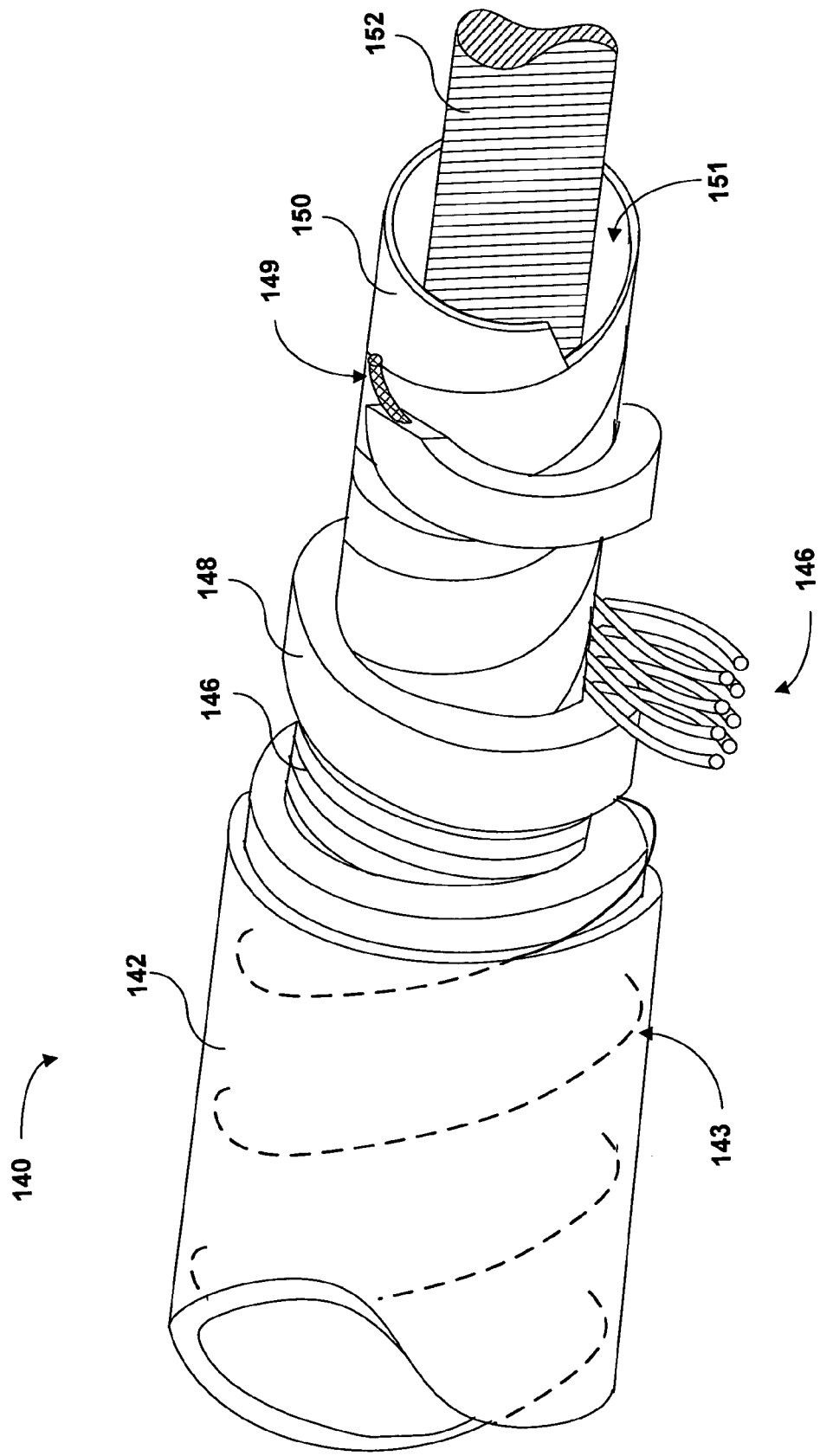
FIG. 9 is a schematic diagram illustrating a cutaway view of another implantable medical lead according to an embodiment of the invention.

FIG. 9 is a schematic diagram illustrating a cutaway view of another implantable stretchable medical lead 140 for use with an implantable medical device according to an embodiment of the invention. Lead 140 includes an outer jacket 142, a helical reinforcement wire 148, conductors 146 and a stylet guide tube 150. For illustrative purposes, stylet 152 is also shown inserted through lumen 151 formed by stylet guide tube 150. Conductors 146 wrap around stylet guide tube 150 in substantial alignment with helical reinforcement wire 148, which includes an embedded wire 149.

Lead 140 is the same as lead 110 in FIG. 8 except that outer jacket 142 includes a coiled wire 143. Coiled wire in outer jacket 142 functions in a similar manner to a wire in a common vacuum cleaner hose. In particular, coiled wire 143 provides structural support to outer jacket 142 while allowing lead 140 to have sufficient flexibility. As lead 140 experiences axial strain, outer jacket 142 elongates under relatively low stresses, but continues to provide structural support to resist bilateral collapse and kinking. Furthermore, the coils of stylet guide tube 150 separate under relatively low stresses, but the cylindrical shape of stylet guide tube 150 is maintained to provide structural support. Stylet guide tube 150 is coiled in an opposite direction of helical reinforcement wire 148 and conductors 146. In the illustrated embodiments, embedded coiled wire 143 within outer jacket 142 is coiled in the same direction as stylet guide tube 150. In other embodiments, embedded coiled wire 143 may be coiled in an opposite direction of stylet guide tube 150.

Embedded coiled wire 143 may be sandwiched between two thin jacket extrusions. For example, outer jacket 142 comprises an inner layer and an outer layer. The inner layer and the outer layer may both comprise urethane. In other cases, the inner layer and the outer layer may both comprise silicone. Coiled wire 143 is embedded in outer jacket 142, between the outer layer and the inner layer. Coiled wire 143 may comprise MP35-N, stainless steel, titanium, titanium alloy, tantalum, tantalum alloy, nitinol or other metals or metallic alloys. Coiled wire 143 may be insulated redundantly by both the inner and outer layer and with a direct insulative coating on the wire 143. While reinforcement wire 143 may not carry a current, insulating wire 143 may decrease the chance that wire 143 could propagate a short among conductors 146.

Placing a coiled wire 143 inside outer jacket 142 will significantly improve column strength and kink resistance. As an example, a 2 to 3 mil wire may be wound around a thin walled inner layer with a large pitch angle, and then an outer layer is extruded over the wire and the inner jacket, thereby producing a composite jacket with a wire reinforcement.

In different embodiments of the invention, an outer jacket that includes an embedded coiled wire, similar to outer jacket 142, may be used with any internal structure of a lead. For example, an outer jacket similar to outer jacket 142 may be used with a lead comprising axial conductors, rather than helical conductors. In some cases, an outer jacket similar to outer jacket 142 may be used with a lead comprising a helical reinforcement as shown in FIG. 7. Similarly, a lead having an outer jacket 142 with an embedded coiled wire 143 may not include a helical reinforcement wire 148 or a coiled wire stylet guide tube 150 as shown in FIG. 9.

Figure 10:
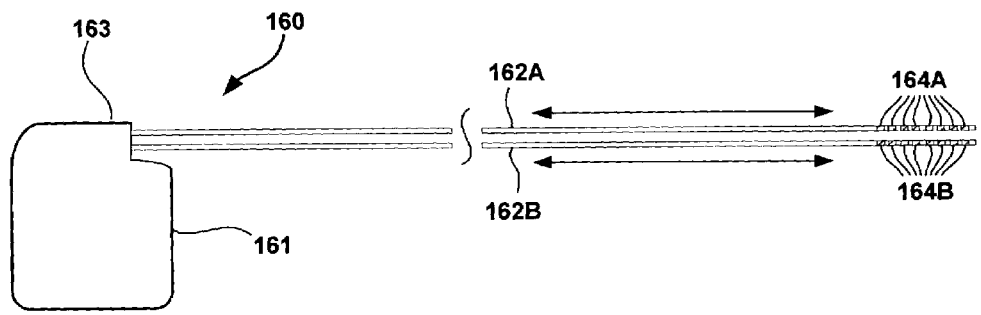
FIG. 10 is a schematic diagram illustrating an implantable medical device for delivering electrical stimulation pulses to a patient.

FIG. 10 is a schematic diagram illustrating an implantable medical device (IMD) 160 for delivering electrical stimulation pulses to a patient. In the example of FIG. 10, IMD 160 includes an IMD housing 161, leads 162A, 162B, and a connector bock 163. Leads 162A, 162B each have a proximal end carrying a set of electrical contacts for connection to reciprocal electrical contacts within connector block 163, and a distal end carrying a set of electrical stimulation electrodes 164A, 164B, respectively. Although two leads 162A, 162B with eight electrodes 164A, 164B each are shown in FIG. 10, a lesser or greater number of leads or electrodes may be used in other embodiments. In general, leads 162A, 162B may be constructed according to any of the embodiments described herein, such that the leads exhibit reduced axial stiffness that permits a degree of stretching when implanted within a patient.

Figure 11:
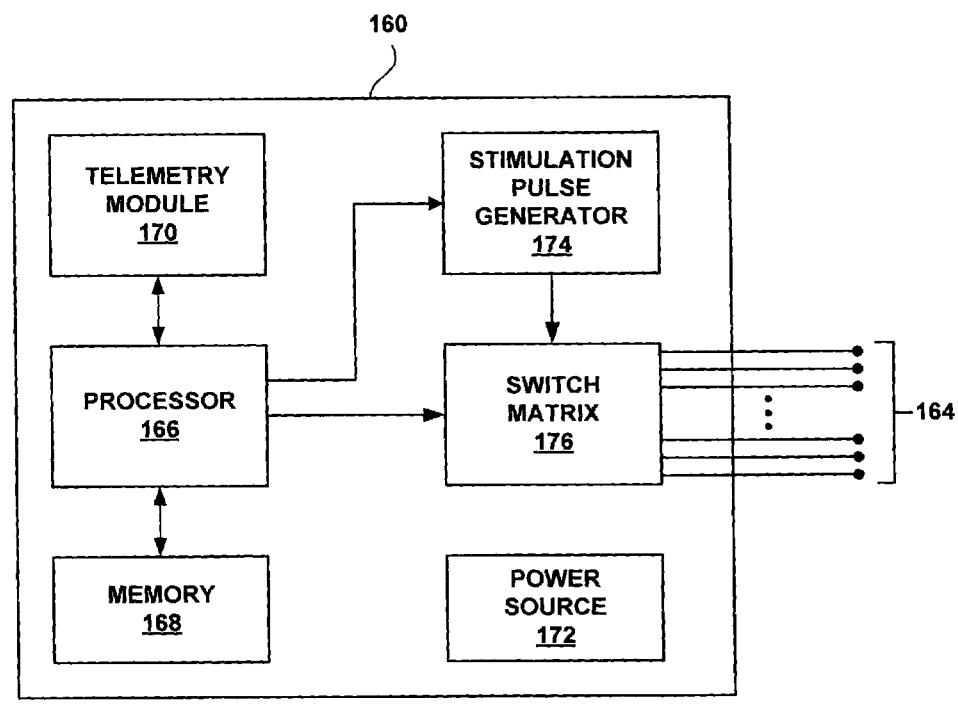
FIG. 11 is a block diagram illustrating components within the device of FIG. 10.

FIG. 11 is a block diagram illustrating components within the IMD housing 161 of FIG. 10. As shown in FIG. 11, IMD housing 161 may include a processor 166, memory 168, telemetry module 170, power source 172, stimulation pulse generator 174, and switch matrix 176. Processor 166 executes instructions stored in memory 168 to control telemetry module 170, stimulation pulse generator 174, and switch matrix 176. In particular, processor 166 controls telemetry module 170 to exchange information with an external programmer by wireless telemetry. Processor 166 specifies stimulation parameters, such as amplitude, pulse, width and pulse rate, for use by stimulation pulse generator 174 in the generation of stimulation pulses for delivery to a patient. Different stimulation parameters may be stored in memory 168 as programs or parameter sets.

The pulses may be delivered via switch matrix 176 and conductors carried by leads 162 and coupled to respective electrodes 164. Processor 166 controls switch matrix to select particular combinations of electrodes 164 for delivery of stimulation pulses generated by stimulation pulse generator 174. For example, electrodes 164 may be combined in various bipolar or multi-polar combinations to deliver stimulation energy to selected sites, such as nerve sites adjacent the spinal column, pelvic floor nerve sites, or cranial nerve sites. The stimulation energy generated by stimulation pulse generator 174 may be formulated as neurostimulation energy, e.g., for treatment of any of a variety of neurological disorders, or disorders influenced by patient neurological response. Alternatively, in other embodiments, stimulation pulse generator 174 could be configured to generate cardiac pacing pulses, or cardioversion/defibrillation shocks.

Power source 172 may take the form of a small, rechargeable or non-rechargeable battery, or an inductive power interface that transcutaneously receives inductively coupled energy. In the case of a rechargeable battery, power source 172 similarly may include an inductive power interface for transcutaneous transfer of recharge power.

Various embodiments of the invention have been described. These and other embodiments are within the scope of the following claims.

The invention claimed is:

1. An implantable medical lead for use with an implantable medical device, the lead comprising:
a lead body that defines a first center axis; multiple conductors located inside the lead body, wherein at least one of the conductors includes a coiled wire defining a lumen with a second center axis substantially parallel to the first center axis of the lead body; and
an extendable fiber disposed within the lumen defined by the coiled wire, wherein the medical lead has an axial stiffness that permits an axial elongation of approximately ten percent to approximately thirty percent without breakage of the medical lead and wherein the fiber limits the coiled wire to an axial stiffness in a range of approximately 0.105 kg/cm/cm to approximately 0.35 kg/cm/cm.

2. The lead of claim 1, further comprising
one or more electrodes at a distal end of the lead body; and
one or more electrical contacts at a proximal end of the lead body,
wherein each of the conductors electrically couples one of the electrodes to one of the electrical contacts.

3. The lead of claim 1, wherein the conductors are formed in tight coils, such that each of the conductors forms a substantially continuous cylindrical shape.

4. The lead of claim 1, wherein the fiber is elastic.

5. The lead of claim 1, wherein the fiber comprises a composite that includes materials selected from the group consisting of fluoropolymer, modified fluoropolymer, polyester, nylon, liquid crystal polymer, modified liquid crystal polymer, or ultra high molecular weight polyethylene.

6. The lead of claim 1, wherein the fiber limits extension of the coiled wire to avoid damage to the coiled wire.

7. The lead of claim 1, wherein the fiber is coupled to a portion of the lead body to limit extension of the lead body.

8. The lead of claim 1, wherein the fiber has an axial stiffness in a range of approximately 0.105 kg/cm/cm to approximately 0.23 kg/cm/cm.

9. The lead of claim 1, wherein the conductors comprise insulated braided silver cored wire.

10. The lead of claim 1, wherein each of the conductors comprise MP35N wire.

11. The lead of claim 1, wherein the conductors comprise braided silver cored wire insulated with a material selected from the group consisting of ethylene-tetrafluoroethylene (ETFE), polytetrafluoroethylene (PTFE), modified PTFE, and polyimide.

12. The lead of claim 1, wherein the coiled wire includes an insulative outer member.

13. The lead of claim 12, wherein the insulative outer member comprises a material selected from the group consisting of polyurethane, silicone, polytetrafluoroethylene (PTFE), polyimide, and polyester.

14. The lead of claim 1, wherein the conductors comprise one or more multi-filar coils.

15. The lead of claim 1, further comprises a stylet guide tube inside the lead body, wherein the conductors are located between the lead body and the stylet guide tube.

16. The lead of claim 15, wherein the stylet guide tube comprises a coiled wire.

17. The lead of claim 14, further comprising a helical reinforcement wound around the stylet guide tube and inside the lead body.

18. The lead of claim 17, wherein the helical reinforcement comprises an insulated wire.

19. The lead of claim 1, further comprising a helical reinforcement inside the lead body, wherein the helical reinforcement comprises a hollow cylindrical shape and a raised helical thread outside the hollow cylindrical shape, wherein the conductors are located between the lead body and the helical reinforcement.

20. The lead of claim 19, further comprising a reinforcement wire embedded within the raised helical thread.

21. The lead of claim 1, wherein the lead body comprises an outer jacket having a first insulative layer, a second insulative layer inside the first insulative layer, and a loosely coiled wire embedded between the first layer and the second layer of the outer jacket.

22. The lead of claim 21, wherein the outer jacket comprises a material selected from the group consisting of polyurethane, silicone, polytetrafluoroethylene (PTFE), modified PTFE, polyimide and polyester.

23. The lead of claim 1, wherein the lead body has a length of approximately 30 to 36 centimeters.

24. The lead of claim 1, wherein the coiled wire defines a lumen that changes in diameter along a length of the lead body from a larger diameter at a proximal end of the lead body to a smaller diameter at a distal end of the lead body.

25. The lead of claim 1, wherein the second center axis of the coiled wire is not coaxial with the first center axis of the lead body.

26. An implantable medical device comprising: a housing;
an implantable pulse generator, within the housing, that generates electrical stimulation pulses; and
an implantable lead, extending from the housing, the implantable lead comprising: a lead body that defines a first center axis, multiple electrodes, multiple conductors located inside the lead body, wherein at least one of the conductors includes a coiled wire defining a lumen with a second center axis substantially parallel to, but not coaxial with, the first center axis of the lead body, and wherein the conductors electrically couple the electrodes to the implantable pulse generator, and
an extendable fiber disposed within the lumen defined by the coiled wire, wherein the medical lead has an axial stiffness that permits an axial elongation of approximately five percent to approximately thirty percent without breakage of the medical lead and wherein the fiber limits the coiled wire to an axial stiffness in a range of approximately 0.105 kg/cm/cm to approximately 0.35 kg/cm/cm.

27. The implantable medical device of claim 26, wherein the conductors are formed in tight coils, such that each of the conductors forms a substantially continuous cylindrical shape.

28. The implantable medical device of claim 26, wherein the fiber comprises a composite that includes materials selected from the group consisting of fluoropolymer, modified fluoropolymer, polyester, nylon, liquid crystal polymer, modified liquid crystal polymer, or ultra high molecular weight polyethylene.

29. The implantable medical device of claim 26, wherein the fiber limits extension of the coiled wire to avoid damage to the coiled wire.

30. The implantable medical device of claim 26, wherein the fiber has an axial stiffness in a range of approximately 0.105 kg/cm/cm to approximately 0.23 kg/cm/cm.

31. The implantable medical device of claim 26, wherein the implantable lead has an axial stiffness that permits an axial elongation of approximately ten percent to approximately thirty percent without breakage of the medical lead.

32. An implantable medical lead comprising: a lead body that defines a center axis, multiple electrodes, multiple conductors located inside the lead body, wherein at least one of the conductors includes a coiled wire defining a lumen with a center axis substantially parallel to the center axis of the lead body, and wherein the conductors electrically couple the electrodes to an implantable pulse generator; and
an extendable fiber disposed within the lumen defined by the coiled wire, wherein the extendable fiber limits the coiled wire to an axial stiffness in a range of approximately 0.105 kg/cm/cm to approximately 0.35 kg/cm/cm.

* * * * *

UNITED STATES PATENT AND TRADEMARK OFFICE
CERTIFICATE OF CORRECTION

PATENT NO. : 7,761,170 B2  Page 1 of 1
APPLICATION NO. : 11/118076
DATED : July 20, 2010
INVENTOR(S) : Paula M. Kaplan It is certified that error appears in the above-identified patent and that said Letters Patent is hereby corrected as shown below:

On the Title Page
Inventor Paula M. Kaplan lives in St. Paul, MN.

In the Claims:

Column 18, line 53, Claim 17
"claim 14" should read -- claim 16 --.

Signed and Sealed this

Ninth Day of November, 2010

David J. Kappos
*Director of the United States Patent and Trademark Office*